US008927208B2

(12) United States Patent
Ter Schegget et al.

(10) Patent No.: US 8,927,208 B2
(45) Date of Patent: Jan. 6, 2015

(54) IDENTIFICATION OF BETA-PAPILLOMAVIRUS DNA BY TYPE-SPECIFIC REVERSE HYBRIDIZATION

(75) Inventors: Jan Ter Schegget, Amsterdam (NL); Maurits Nicholaas Cornelis De Koning, Leiden (NL); Gijsbertus Everardus Maria Kleter, Den Haag (NL); Wilhelmus Gregorius Vincentius Quint, Nootdorp (NL); Jan Lindeman, Bunnik (NL)

(73) Assignee: Labo Bio-Medical Investments B.V., Nootdorp (NL)

( * ) Notice: Subject to any disclaimer, the term of this patent is extended or adjusted under 35 U.S.C. 154(b) by 1450 days.

(21) Appl. No.: 11/909,977

(22) PCT Filed: Mar. 30, 2006

(86) PCT No.: PCT/NL2006/000163
§ 371 (c)(1),
(2), (4) Date: Jun. 23, 2008

(87) PCT Pub. No.: WO2006/104381
PCT Pub. Date: Oct. 5, 2006

(65) Prior Publication Data
US 2009/0170080 A1    Jul. 2, 2009

(30) Foreign Application Priority Data
Mar. 30, 2005    (EP) .................................. 05075742

(51) Int. Cl.
C12Q 1/68    (2006.01)
C12P 19/34    (2006.01)
C07H 21/02    (2006.01)
C07H 21/04    (2006.01)
C12Q 1/70    (2006.01)

(52) U.S. Cl.
CPC .......... *C12Q 1/708* (2013.01); *C12Q 2600/156* (2013.01)
USPC ........................... 435/6.1; 435/91.1; 536/24.3

(58) Field of Classification Search
None
See application file for complete search history.

(56) References Cited

U.S. PATENT DOCUMENTS

| 5,457,189 | A  | * | 10/1995 | Crooke et al. ............... 536/24.5 |
| 6,391,539 | B1 | * | 5/2002  | Orth et al. .......................... 435/5 |
| 6,582,908 | B2 | * | 6/2003  | Fodor et al. ....................... 506/9 |
| 2003/0082551 | A1 | * | 5/2003  | Zarling et al. .................... 435/6 |
| 2003/0129585 | A1 | * | 7/2003  | Iftner ................................. 435/5 |
| 2003/0165821 | A1 |   | 9/2003  | Van Doorn et al. |
| 2005/0175987 | A1 | * | 8/2005  | Jansen et al. ...................... 435/5 |

FOREIGN PATENT DOCUMENTS

WO    WO-03/087829    10/2003

OTHER PUBLICATIONS

Klaassen, Corne H et al. DNA microarray format for detection and subtyping of human papillomavirus. Journal of Clinical Microbiology. May 2004 vol. 42 No. 5 pp. 2152-2160.*
de Villiers, Ethel-Michele et al. Classification of papillomaviruses. Virology 2004 vol. 324 pp. 17-27.*
International Search Report for PCT/NL2006/000163, mailed on Aug. 29, 2006, 3 pages.
Koning et al., Journal of Clinical Microbiology (2006) 44:1792-1800.
Molijn et al., Journal of Clinical Virology (2005) 32S:S43-S51.
Tieben et al., Journal of Virological Methods (1993) 42:265-280.

* cited by examiner

*Primary Examiner* — Jehanne Sitton
(74) *Attorney, Agent, or Firm* — Morrison & Foerster LLP

(57) ABSTRACT

The invention provides new probes that are useful in a method to analyze beta-PV types based on hybridization to these probes.

13 Claims, 5 Drawing Sheets

Figure 1.
Nucleotide sequence alignment of the target region for the universal probes and the probes for 25 beta-PV types. The sequence numbering is related to the HPV 5 sequence PPH5CG and nucleotides identical to the top sequence are indicated as dots. The complete 83 bp area is designated as region A. Region B is the target for the universal probes.

Outline of the HPV genome. Relative to the position on the HPV genome the HPV genes and the A and B regions are depicted (see also Figure 1).

Phylogenetic tree of region A from 25 beta-PV genotypes.

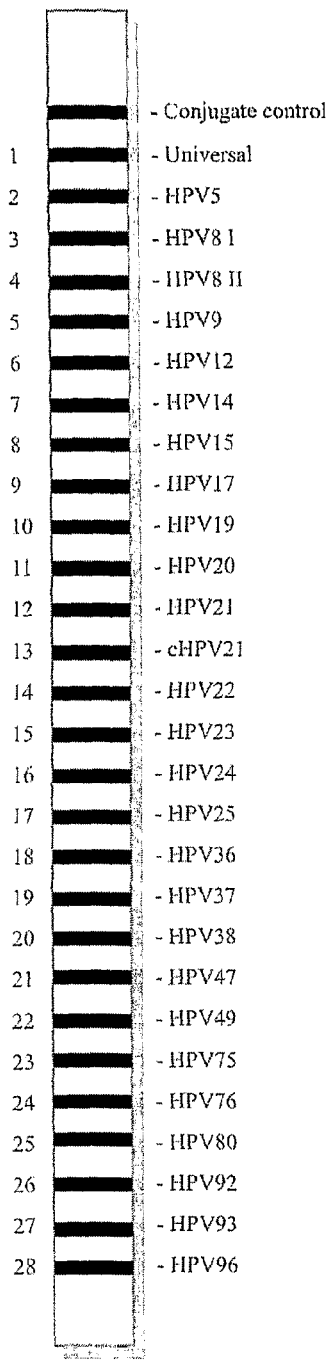

Figure 4. Outline of the skin (beta) HPV genotyping strip.
A possible make-up for the strip that enables detection and identification of 25 beta-PV genotypes is shown. The lines correspond to the positions of the probes and the names of the probes are from Table 1. "Universal" indicates the position where the 4 universal probes are applied (Table 2). Biotinylated poly(dT)$_{40}$ serves as a positive control for the conjugate and substrate reaction and is designated as "Conjugate control".

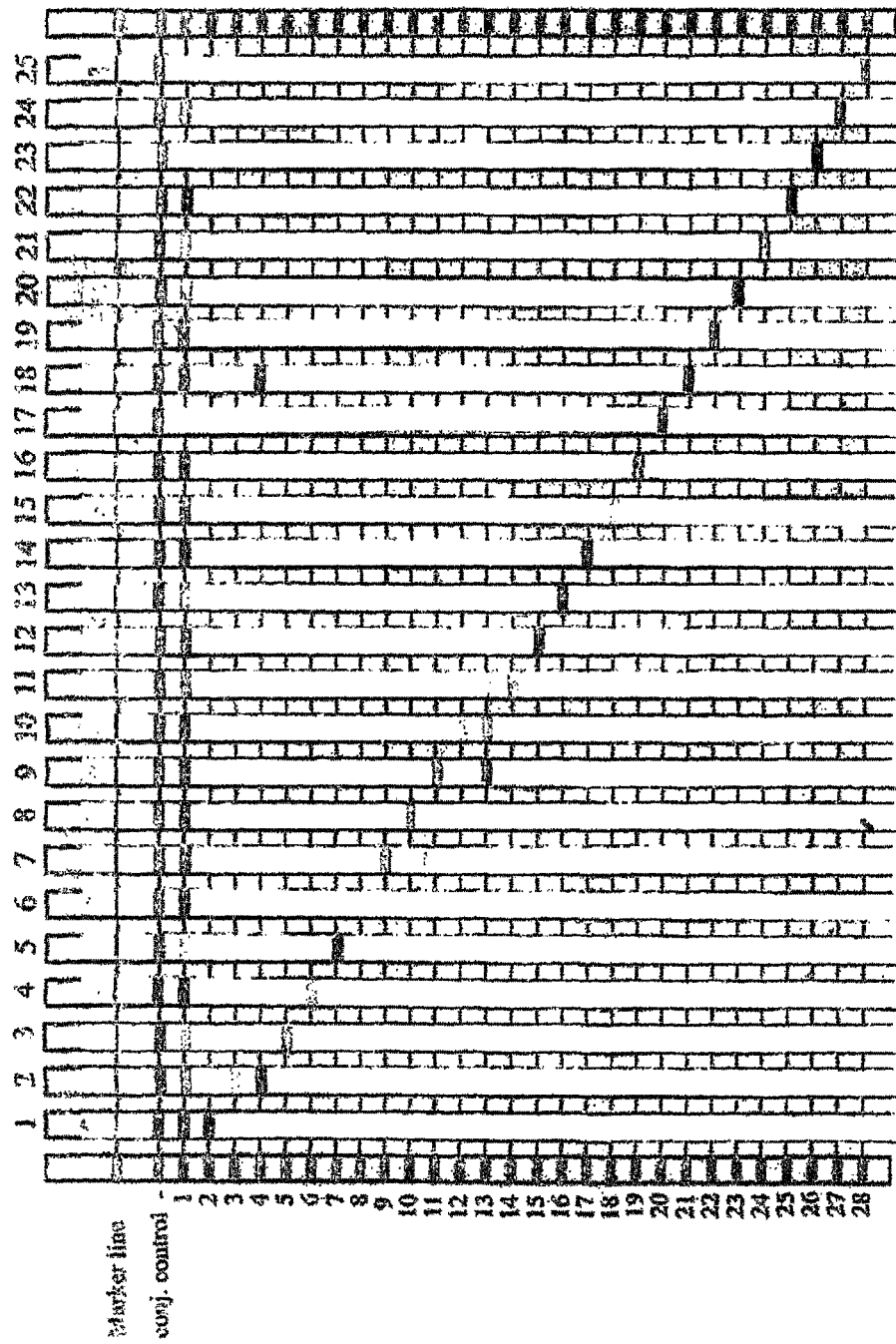
Figure 5. Typical patterns arising upon analysis of amplimers with the skin (beta) HPV genotyping strip. The amplimers were obtained by performing PCR on plasmid clones of 23 beta-PV genotypes and 2 beta candPV genotypes (genotyping results representing HPV types 5, 8, 9, 12, 14, 15, 17, 19-25, 36-38, 47, 49, 75, 76, 80, 92, 93, and 96 are shown from respectively strip 1 to 25).

SEQUENCE LISTING

```
<160> NUMBER OF SEQ ID NOS: 127

<210> SEQ ID NO 1
<211> LENGTH: 16
<212> TYPE: DNA
<213> ORGANISM: Artificial Sequence
<220> FEATURE:
<223> OTHER INFORMATION: Probe HPV12

<400> SEQUENCE: 1
gccaacatgg agaatc                                                     16

<210> SEQ ID NO 2
<211> LENGTH: 17
<212> TYPE: DNA
<213> ORGANISM: Artificial Sequence
<220> FEATURE:
<223> OTHER INFORMATION: Probe HPV14

<400> SEQUENCE: 2
gggagacaat ggagaat                                                    17

<210> SEQ ID NO 3
<211> LENGTH: 20
<212> TYPE: DNA
<213> ORGANISM: Artificial Sequence
<220> FEATURE:
<223> OTHER INFORMATION: Probe 15 EV PR1

<400> SEQUENCE: 3
gacagttaga gctcagtgat                                                 20

<210> SEQ ID NO 4
<211> LENGTH: 20
<212> TYPE: DNA
```

```
<213> ORGANISM: Artificial Sequence
<220> FEATURE:
<223> OTHER INFORMATION: Probe 15 EV PR2

<400> SEQUENCE: 4
gacagttaga gctcagtgat                                              20

<210> SEQ ID NO 5
<211> LENGTH: 19
<212> TYPE: DNA
<213> ORGANISM: Artificial Sequence
<220> FEATURE:
<223> OTHER INFORMATION: Probe 15 EV PR3

<400> SEQUENCE: 5
agacagttag agctcagtg                                               19

<210> SEQ ID NO 6
<211> LENGTH: 19
<212> TYPE: DNA
<213> ORGANISM: Artificial Sequence
<220> FEATURE:
<223> OTHER INFORMATION: Probe 15 EV PR4

<400> SEQUENCE: 6
gagacagtta gagctcagt                                               19

<210> SEQ ID NO 7
<211> LENGTH: 19
<212> TYPE: DNA
<213> ORGANISM: Artificial Sequence
<220> FEATURE:
<223> OTHER INFORMATION: Probe 15 EV PR5

<400> SEQUENCE: 7
gagacagtta gagctcagc                                               19

<210> SEQ ID NO 8
<211> LENGTH: 17
<212> TYPE: DNA
<213> ORGANISM: Artificial Sequence
<220> FEATURE:
<223> OTHER INFORMATION: Probe 15 EV PR6

<400> SEQUENCE: 8
gagacagtta gagctca                                                 17

<210> SEQ ID NO 9
<211> LENGTH: 17
<212> TYPE: DNA
<213> ORGANISM: Artificial Sequence
<220> FEATURE:
<223> OTHER INFORMATION: Probe 15 EV PR7

<400> SEQUENCE: 9
agacagttag agctcag                                                 17

<210> SEQ ID NO 10
<211> LENGTH: 16
<212> TYPE: DNA
<213> ORGANISM: Artificial Sequence
<220> FEATURE:
<223> OTHER INFORMATION: Probe HPV15

<400> SEQUENCE: 10
agacagttag agctca                                                  16
```

<210> SEQ ID NO 11
<211> LENGTH: 19
<212> TYPE: DNA
<213> ORGANISM: Artificial Sequence
<220> FEATURE:
<223> OTHER INFORMATION: Probe HPV17

<400> SEQUENCE: 11
ggcatcagtt agatctgag                                                  19

<210> SEQ ID NO 12
<211> LENGTH: 18
<212> TYPE: DNA
<213> ORGANISM: Artificial Sequence
<220> FEATURE:
<223> OTHER INFORMATION: Probe HPV19

<400> SEQUENCE: 12
tggcaacaat tagaactg                                                   18

<210> SEQ ID NO 13
<211> LENGTH: 19
<212> TYPE: DNA
<213> ORGANISM: Artificial Sequence
<220> FEATURE:
<223> OTHER INFORMATION: Probe 20 EV PR1

<400> SEQUENCE: 13
gaagcaatta gagctgagt                                                  19

<210> SEQ ID NO 14
<211> LENGTH: 19
<212> TYPE: DNA
<213> ORGANISM: Artificial Sequence
<220> FEATURE:
<223> OTHER INFORMATION: Probe 20 EV PR2

<400> SEQUENCE: 14
gaagcaatta gagctgagg                                                  19

<210> SEQ ID NO 15
<211> LENGTH: 18
<212> TYPE: DNA
<213> ORGANISM: Artificial Sequence
<220> FEATURE:
<223> OTHER INFORMATION: Probe 20 EV PR3

<400> SEQUENCE: 15
tggaagcaat tagagctg                                                   18

<210> SEQ ID NO 16
<211> LENGTH: 17
<212> TYPE: DNA
<213> ORGANISM: Artificial Sequence
<220> FEATURE:
<223> OTHER INFORMATION: Probe HPV20

<400> SEQUENCE: 16
ggaagcaatt agagctg                                                    17

<210> SEQ ID NO 17
<211> LENGTH: 16
<212> TYPE: DNA
<213> ORGANISM: Artificial Sequence
<220> FEATURE:

```
<223> OTHER INFORMATION: Probe 21 EV PR1

<400> SEQUENCE: 17
gaatctcagc gatcgt                                                        16

<210> SEQ ID NO 18
<211> LENGTH: 18
<212> TYPE: DNA
<213> ORGANISM: Artificial Sequence
<220> FEATURE:
<223> OTHER INFORMATION: Probe 21 EV PR2

<400> SEQUENCE: 18
gaatctcagc gatcgtgg                                                      18

<210> SEQ ID NO 19
<211> LENGTH: 18
<212> TYPE: DNA
<213> ORGANISM: Artificial Sequence
<220> FEATURE:
<223> OTHER INFORMATION: Probe 21 EV PR3

<400> SEQUENCE: 19
gaatctcagc gatcgttg                                                      18

<210> SEQ ID NO 20
<211> LENGTH: 18
<212> TYPE: DNA
<213> ORGANISM: Artificial Sequence
<220> FEATURE:
<223> OTHER INFORMATION: Probe 21 EV PRX RC

<400> SEQUENCE: 20
attctccatt ttctcccg                                                      18

<210> SEQ ID NO 21
<211> LENGTH: 17
<212> TYPE: DNA
<213> ORGANISM: Artificial Sequence
<220> FEATURE:
<223> OTHER INFORMATION: Probe cHPV21

<400> SEQUENCE: 21
attctccatt ttctccc                                                       17

<210> SEQ ID NO 22
<211> LENGTH: 18
<212> TYPE: DNA
<213> ORGANISM: Artificial Sequence
<220> FEATURE:
<223> OTHER INFORMATION: Probe HPV21

<400> SEQUENCE: 22
gaatctcagc gatcgggg                                                      18

<210> SEQ ID NO 23
<211> LENGTH: 19
<212> TYPE: DNA
<213> ORGANISM: Artificial Sequence
<220> FEATURE:
<223> OTHER INFORMATION: Probe 21 EV PR12

<400> SEQUENCE: 23
agaatctcag cgatccggg                                                     19
```

```
<210> SEQ ID NO 24
<211> LENGTH: 16
<212> TYPE: DNA
<213> ORGANISM: Artificial Sequence
<220> FEATURE:
<223> OTHER INFORMATION: Probe 21 EV PR11 RC

<400> SEQUENCE: 24
cgatcgctga gattcc                                                   16

<210> SEQ ID NO 25
<211> LENGTH: 15
<212> TYPE: DNA
<213> ORGANISM: Artificial Sequence
<220> FEATURE:
<223> OTHER INFORMATION: Probe 21 EV PR12 RC

<400> SEQUENCE: 25
gatcgctgag attct                                                    15

<210> SEQ ID NO 26
<211> LENGTH: 17
<212> TYPE: DNA
<213> ORGANISM: Artificial Sequence
<220> FEATURE:
<223> OTHER INFORMATION: Probe 21 EV PR13 RC

<400> SEQUENCE: 26
acgatcgctg agattcc                                                  17

<210> SEQ ID NO 27
<211> LENGTH: 18
<212> TYPE: DNA
<213> ORGANISM: Artificial Sequence
<220> FEATURE:
<223> OTHER INFORMATION: Probe 21 EV PR14 RC

<400> SEQUENCE: 27
aacgatcgct gagattcc                                                 18

<210> SEQ ID NO 28
<211> LENGTH: 17
<212> TYPE: DNA
<213> ORGANISM: Artificial Sequence
<220> FEATURE:
<223> OTHER INFORMATION: Probe 21 EV prX

<400> SEQUENCE: 28
gggagaaaat ggagaat                                                  17

<210> SEQ ID NO 29
<211> LENGTH: 19
<212> TYPE: DNA
<213> ORGANISM: Artificial Sequence
<220> FEATURE:
<223> OTHER INFORMATION: Probe HPV22

<400> SEQUENCE: 29
gagaaaatgg agaaactca                                                19

<210> SEQ ID NO 30
<211> LENGTH: 20
<212> TYPE: DNA
<213> ORGANISM: Artificial Sequence
<220> FEATURE:
<223> OTHER INFORMATION: Probe HPV23
```

```
<400> SEQUENCE: 30
tggatacaat taggactcag                                            20

<210> SEQ ID NO 31
<211> LENGTH: 17
<212> TYPE: DNA
<213> ORGANISM: Artificial Sequence
<220> FEATURE:
<223> OTHER INFORMATION: Probe 24 EV PR1

<400> SEQUENCE: 31
agaggatgga gaacctg                                               17

<210> SEQ ID NO 32
<211> LENGTH: 18
<212> TYPE: DNA
<213> ORGANISM: Artificial Sequence
<220> FEATURE:
<223> OTHER INFORMATION: Probe HPV24

<400> SEQUENCE: 32
gagaggatgg agaacctg                                              18

<210> SEQ ID NO 33
<211> LENGTH: 18
<212> TYPE: DNA
<213> ORGANISM: Artificial Sequence
<220> FEATURE:
<223> OTHER INFORMATION: Probe 24 EV PR3

<400> SEQUENCE: 33
agaggatgga gaacctga                                              18

<210> SEQ ID NO 34
<211> LENGTH: 17
<212> TYPE: DNA
<213> ORGANISM: Artificial Sequence
<220> FEATURE:
<223> OTHER INFORMATION: Probe 25 EV PR1

<400> SEQUENCE: 34
ggcatcaatt agacctg                                               17

<210> SEQ ID NO 35
<211> LENGTH: 18
<212> TYPE: DNA
<213> ORGANISM: Artificial Sequence
<220> FEATURE:
<223> OTHER INFORMATION: Probe HPV25

<400> SEQUENCE: 35
tggcatcaat tagacctg                                              18

<210> SEQ ID NO 36
<211> LENGTH: 18
<212> TYPE: DNA
<213> ORGANISM: Artificial Sequence
<220> FEATURE:
<223> OTHER INFORMATION: Probe 25 EV PR3

<400> SEQUENCE: 36
ggcatcaatt agacctga                                              18

<210> SEQ ID NO 37
<211> LENGTH: 19
```

```
<212> TYPE: DNA
<213> ORGANISM: Artificial Sequence
<220> FEATURE:
<223> OTHER INFORMATION: Probe 36 EV PR1

<400> SEQUENCE: 37
gaactcagtg accaagaag                                          19

<210> SEQ ID NO 38
<211> LENGTH: 18
<212> TYPE: DNA
<213> ORGANISM: Artificial Sequence
<220> FEATURE:
<223> OTHER INFORMATION: Probe 36 EV PR2

<400> SEQUENCE: 38
gaactcagtg accaagaa                                           18

<210> SEQ ID NO 39
<211> LENGTH: 18
<212> TYPE: DNA
<213> ORGANISM: Artificial Sequence
<220> FEATURE:
<223> OTHER INFORMATION: Probe 36 EV PR3

<400> SEQUENCE: 39
agaactcagt gaccaaga                                           18

<210> SEQ ID NO 40
<211> LENGTH: 17
<212> TYPE: DNA
<213> ORGANISM: Artificial Sequence
<220> FEATURE:
<223> OTHER INFORMATION: Probe 36 EV PR4

<400> SEQUENCE: 40
gaactcagtg accaaga                                            17

<210> SEQ ID NO 41
<211> LENGTH: 16
<212> TYPE: DNA
<213> ORGANISM: Artificial Sequence
<220> FEATURE:
<223> OTHER INFORMATION: Probe 36 EV PR11

<400> SEQUENCE: 41
gaactcagtg accaag                                             16

<210> SEQ ID NO 42
<211> LENGTH: 16
<212> TYPE: DNA
<213> ORGANISM: Artificial Sequence
<220> FEATURE:
<223> OTHER INFORMATION: Probe 36 EV PR12

<400> SEQUENCE: 42
agaactcagt gaccaa                                             16

<210> SEQ ID NO 43
<211> LENGTH: 17
<212> TYPE: DNA
<213> ORGANISM: Artificial Sequence
<220> FEATURE:
<223> OTHER INFORMATION: Probe HPV36

<400> SEQUENCE: 43
```
tagaactcag tgaccaa						17

<210> SEQ ID NO 44
<211> LENGTH: 19
<212> TYPE: DNA
<213> ORGANISM: Artificial Sequence
<220> FEATURE:
<223> OTHER INFORMATION: Probe 37 EV PR1

<400> SEQUENCE: 44
gatctcagtg accaagaag					19

<210> SEQ ID NO 45
<211> LENGTH: 18
<212> TYPE: DNA
<213> ORGANISM: Artificial Sequence
<220> FEATURE:
<223> OTHER INFORMATION: Probe 37 EV PR2

<400> SEQUENCE: 45
gatctcagtg accaagaa					18

<210> SEQ ID NO 46
<211> LENGTH: 18
<212> TYPE: DNA
<213> ORGANISM: Artificial Sequence
<220> FEATURE:
<223> OTHER INFORMATION: Probe 37 EV PR3

<400> SEQUENCE: 46
agatctcagt gaccaaga					18

<210> SEQ ID NO 47
<211> LENGTH: 17
<212> TYPE: DNA
<213> ORGANISM: Artificial Sequence
<220> FEATURE:
<223> OTHER INFORMATION: Probe 37 EV PR4

<400> SEQUENCE: 47
gatctcagtg accaaga					17

<210> SEQ ID NO 48
<211> LENGTH: 16
<212> TYPE: DNA
<213> ORGANISM: Artificial Sequence
<220> FEATURE:
<223> OTHER INFORMATION: Probe HPV37

<400> SEQUENCE: 48
gatctcagtg accaag					16

<210> SEQ ID NO 49
<211> LENGTH: 16
<212> TYPE: DNA
<213> ORGANISM: Artificial Sequence
<220> FEATURE:
<223> OTHER INFORMATION: Probe 37 EV PR12

<400> SEQUENCE: 49
agatctcagt gaccaa					16

<210> SEQ ID NO 50
<211> LENGTH: 17
<212> TYPE: DNA
<213> ORGANISM: Artificial Sequence

```
<220> FEATURE:
<223> OTHER INFORMATION: Probe 37 EV PR13

<400> SEQUENCE: 50
tagatctcag tgaccaa                                                  17

<210> SEQ ID NO 51
<211> LENGTH: 17
<212> TYPE: DNA
<213> ORGANISM: Artificial Sequence
<220> FEATURE:
<223> OTHER INFORMATION: Probe HPV38

<400> SEQUENCE: 51
gggagacaat ggaaact                                                  17

<210> SEQ ID NO 52
<211> LENGTH: 18
<212> TYPE: DNA
<213> ORGANISM: Artificial Sequence
<220> FEATURE:
<223> OTHER INFORMATION: Probe HPV47

<400> SEQUENCE: 52
tggacacact tagacctg                                                 18

<210> SEQ ID NO 53
<211> LENGTH: 20
<212> TYPE: DNA
<213> ORGANISM: Artificial Sequence
<220> FEATURE:
<223> OTHER INFORMATION: Probe 47 EV PR1.CH

<400> SEQUENCE: 53
gctggacaca cttagacctg                                               20

<210> SEQ ID NO 54
<211> LENGTH: 19
<212> TYPE: DNA
<213> ORGANISM: Artificial Sequence
<220> FEATURE:
<223> OTHER INFORMATION: Probe 47 EV PR1RC.CH

<400> SEQUENCE: 54
gcaggtctaa gtgtgtcca                                                19

<210> SEQ ID NO 55
<211> LENGTH: 20
<212> TYPE: DNA
<213> ORGANISM: Artificial Sequence
<220> FEATURE:
<223> OTHER INFORMATION: Probe 47 EV PR2.CH

<400> SEQUENCE: 55
gcgggacaca cttagacctg                                               20

<210> SEQ ID NO 56
<211> LENGTH: 19
<212> TYPE: DNA
<213> ORGANISM: Artificial Sequence
<220> FEATURE:
<223> OTHER INFORMATION: Probe 47 EV PR3.CH

<400> SEQUENCE: 56
gctggacaca cttagacct                                                19
```

<210> SEQ ID NO 57
<211> LENGTH: 16
<212> TYPE: DNA
<213> ORGANISM: Artificial Sequence
<220> FEATURE:
<223> OTHER INFORMATION: Probe 49 EV PR1

<400> SEQUENCE: 57
gagctcagtg acccag                                                     16

<210> SEQ ID NO 58
<211> LENGTH: 15
<212> TYPE: DNA
<213> ORGANISM: Artificial Sequence
<220> FEATURE:
<223> OTHER INFORMATION: Probe 49 EV PR10

<400> SEQUENCE: 58
gaggcactca acgct                                                      15

<210> SEQ ID NO 59
<211> LENGTH: 15
<212> TYPE: DNA
<213> ORGANISM: Artificial Sequence
<220> FEATURE:
<223> OTHER INFORMATION: Probe 49 EV PR11

<400> SEQUENCE: 59
aggcactcaa cgctc                                                      15

<210> SEQ ID NO 60
<211> LENGTH: 18
<212> TYPE: DNA
<213> ORGANISM: Artificial Sequence
<220> FEATURE:
<223> OTHER INFORMATION: Probe HPV49

<400> SEQUENCE: 60
aggcactcaa cgctctgg                                                   18

<210> SEQ ID NO 61
<211> LENGTH: 18
<212> TYPE: DNA
<213> ORGANISM: Artificial Sequence
<220> FEATURE:
<223> OTHER INFORMATION: Probe HPV5

<400> SEQUENCE: 61
gacctgagtg atcaagaa                                                   18

<210> SEQ ID NO 62
<211> LENGTH: 21
<212> TYPE: DNA
<213> ORGANISM: Artificial Sequence
<220> FEATURE:
<223> OTHER INFORMATION: Probe 5 EV PR2.CH

<400> SEQUENCE: 62
ggggacctga gtgatcaaga a                                               21

<210> SEQ ID NO 63
<211> LENGTH: 18
<212> TYPE: DNA
<213> ORGANISM: Artificial Sequence
<220> FEATURE:
<223> OTHER INFORMATION: Probe 5 EV PR3

```
<400> SEQUENCE: 63
agacctgagt gatcaaga                                           18

<210> SEQ ID NO 64
<211> LENGTH: 19
<212> TYPE: DNA
<213> ORGANISM: Artificial Sequence
<220> FEATURE:
<223> OTHER INFORMATION: Probe 5 EV PR1

<400> SEQUENCE: 64
gacctgagtg atcaagaag                                          19

<210> SEQ ID NO 65
<211> LENGTH: 20
<212> TYPE: DNA
<213> ORGANISM: Artificial Sequence
<220> FEATURE:
<223> OTHER INFORMATION: Probe 5 EV PR2RC.CH

<400> SEQUENCE: 65
gtttcttgat cactcaggtc                                         20

<210> SEQ ID NO 66
<211> LENGTH: 20
<212> TYPE: DNA
<213> ORGANISM: Artificial Sequence
<220> FEATURE:
<223> OTHER INFORMATION: Probe 5 EV PR4.CH

<400> SEQUENCE: 66
ggggacctga gtgatcaaga                                         20

<210> SEQ ID NO 67
<211> LENGTH: 21
<212> TYPE: DNA
<213> ORGANISM: Artificial Sequence
<220> FEATURE:
<223> OTHER INFORMATION: Probe 5EV PR5.CH

<400> SEQUENCE: 67
gggcacctga gtgatcaaga a                                       21

<210> SEQ ID NO 68
<211> LENGTH: 19
<212> TYPE: DNA
<213> ORGANISM: Artificial Sequence
<220> FEATURE:
<223> OTHER INFORMATION: Probe HPV75

<400> SEQUENCE: 68
gaactgagtg atcctgaag                                          19

<210> SEQ ID NO 69
<211> LENGTH: 18
<212> TYPE: DNA
<213> ORGANISM: Artificial Sequence
<220> FEATURE:
<223> OTHER INFORMATION: Probe HPV76

<400> SEQUENCE: 69
agatctcagt gaccctga                                           18

<210> SEQ ID NO 70
```

<211> LENGTH: 19
<212> TYPE: DNA
<213> ORGANISM: Artificial Sequence
<220> FEATURE:
<223> OTHER INFORMATION: Probe 8 EV PR4

<400> SEQUENCE: 70
attagagctg agtgatcag                                              19

<210> SEQ ID NO 71
<211> LENGTH: 18
<212> TYPE: DNA
<213> ORGANISM: Artificial Sequence
<220> FEATURE:
<223> OTHER INFORMATION: Probe HPV8 I

<400> SEQUENCE: 71
ttagagctga gtgatcag                                               18

<210> SEQ ID NO 72
<211> LENGTH: 17
<212> TYPE: DNA
<213> ORGANISM: Artificial Sequence
<220> FEATURE:
<223> OTHER INFORMATION: Probe 8 EV PR5.CH

<400> SEQUENCE: 72
ttagagctga gtgatca                                                17

<210> SEQ ID NO 73
<211> LENGTH: 21
<212> TYPE: DNA
<213> ORGANISM: Artificial Sequence
<220> FEATURE:
<223> OTHER INFORMATION: Probe 8 EV PR5RC.CH

<400> SEQUENCE: 73
ggtctgatca ctcagctcta a                                           21

<210> SEQ ID NO 74
<211> LENGTH: 16
<212> TYPE: DNA
<213> ORGANISM: Artificial Sequence
<220> FEATURE:
<223> OTHER INFORMATION: Probe 8 EV PR6.CH

<400> SEQUENCE: 74
ttagagctga gtgatc                                                 16

<210> SEQ ID NO 75
<211> LENGTH: 17
<212> TYPE: DNA
<213> ORGANISM: Artificial Sequence
<220> FEATURE:
<223> OTHER INFORMATION: Probe 8 EV PR7.CH

<400> SEQUENCE: 75
gtagagctga gtgatca                                                17

<210> SEQ ID NO 76
<211> LENGTH: 20
<212> TYPE: DNA
<213> ORGANISM: Artificial Sequence
<220> FEATURE:
<223> OTHER INFORMATION: Probe 8 EV PR1

<400> SEQUENCE: 76

```
attagagctg agtgatcaag                                              20

<210> SEQ ID NO 77
<211> LENGTH: 19
<212> TYPE: DNA
<213> ORGANISM: Artificial Sequence
<220> FEATURE:
<223> OTHER INFORMATION: Probe 8 EV PR10

<400> SEQUENCE: 77
acacaattag agctgagtg                                               19

<210> SEQ ID NO 78
<211> LENGTH: 20
<212> TYPE: DNA
<213> ORGANISM: Artificial Sequence
<220> FEATURE:
<223> OTHER INFORMATION: Probe 8 EV PR11

<400> SEQUENCE: 78
cacacaatta gagctgagtg                                              20

<210> SEQ ID NO 79
<211> LENGTH: 18
<212> TYPE: DNA
<213> ORGANISM: Artificial Sequence
<220> FEATURE:
<223> OTHER INFORMATION: Probe 8 EV PR12

<400> SEQUENCE: 79
cacaattaga gctgagtg                                                18

<210> SEQ ID NO 80
<211> LENGTH: 17
<212> TYPE: DNA
<213> ORGANISM: Artificial Sequence
<220> FEATURE:
<223> OTHER INFORMATION: Probe 8 EV PR13

<400> SEQUENCE: 80
cacaattaga gctgagt                                                 17

<210> SEQ ID NO 81
<211> LENGTH: 18
<212> TYPE: DNA
<213> ORGANISM: Artificial Sequence
<220> FEATURE:
<223> OTHER INFORMATION: Probe 8 EV PR14

<400> SEQUENCE: 81
acacaattag agctgagt                                                18

<210> SEQ ID NO 82
<211> LENGTH: 18
<212> TYPE: DNA
<213> ORGANISM: Artificial Sequence
<220> FEATURE:
<223> OTHER INFORMATION: Probe 8 EV PR15

<400> SEQUENCE: 82
acacaattag agctgagg                                                18

<210> SEQ ID NO 83
<211> LENGTH: 19
<212> TYPE: DNA
```

```
<213> ORGANISM: Artificial Sequence
<220> FEATURE:
<223> OTHER INFORMATION: Probe 8 EV PR2

<400> SEQUENCE: 83
attagagctg agtgatcaa                                                       19

<210> SEQ ID NO 84
<211> LENGTH: 19
<212> TYPE: DNA
<213> ORGANISM: Artificial Sequence
<220> FEATURE:
<223> OTHER INFORMATION: Probe 8 EV PR3

<400> SEQUENCE: 84
ttagagctga gtgatcaag                                                       19

<210> SEQ ID NO 85
<211> LENGTH: 17
<212> TYPE: DNA
<213> ORGANISM: Artificial Sequence
<220> FEATURE:
<223> OTHER INFORMATION: Probe HPV8 II

<400> SEQUENCE: 85
gcgaacatgg agaatct                                                         17

<210> SEQ ID NO 86
<211> LENGTH: 17
<212> TYPE: DNA
<213> ORGANISM: Artificial Sequence
<220> FEATURE:
<223> OTHER INFORMATION: Probe 8 EV PRX2

<400> SEQUENCE: 86
gcgaacatgg agaatcg                                                         17

<210> SEQ ID NO 87
<211> LENGTH: 19
<212> TYPE: DNA
<213> ORGANISM: Artificial Sequence
<220> FEATURE:
<223> OTHER INFORMATION: Probe 8 EV PR12 RC

<400> SEQUENCE: 87
cactcagctc taattgtgc                                                       19

<210> SEQ ID NO 88
<211> LENGTH: 18
<212> TYPE: DNA
<213> ORGANISM: Artificial Sequence
<220> FEATURE:
<223> OTHER INFORMATION: Probe 8 EV PR5 RC

<400> SEQUENCE: 88
tgatcactca gctctaag                                                        18

<210> SEQ ID NO 89
<211> LENGTH: 19
<212> TYPE: DNA
<213> ORGANISM: Artificial Sequence
<220> FEATURE:
<223> OTHER INFORMATION: Probe HPV80

<400> SEQUENCE: 89
tagatctcag tgatcacga                                                       19
```

<210> SEQ ID NO 90
<211> LENGTH: 18
<212> TYPE: DNA
<213> ORGANISM: Artificial Sequence
<220> FEATURE:
<223> OTHER INFORMATION: Probe HPV9

<400> SEQUENCE: 90
gaggatggaa actctcag                                                  18

<210> SEQ ID NO 91
<211> LENGTH: 15
<212> TYPE: DNA
<213> ORGANISM: Artificial Sequence
<220> FEATURE:
<223> OTHER INFORMATION: Probe 92 EV PR1

<400> SEQUENCE: 91
caaaggcttt ggagg                                                     15

<210> SEQ ID NO 92
<211> LENGTH: 15
<212> TYPE: DNA
<213> ORGANISM: Artificial Sequence
<220> FEATURE:
<223> OTHER INFORMATION: Probe 92 EV PR10

<400> SEQUENCE: 92
cgagggtgag gatgg                                                     15

<210> SEQ ID NO 93
<211> LENGTH: 15
<212> TYPE: DNA
<213> ORGANISM: Artificial Sequence
<220> FEATURE:
<223> OTHER INFORMATION: Probe HPV92

<400> SEQUENCE: 93
aggctctcag cgacc                                                     15

<210> SEQ ID NO 94
<211> LENGTH: 17
<212> TYPE: DNA
<213> ORGANISM: Artificial Sequence
<220> FEATURE:
<223> OTHER INFORMATION: Probe HPV93

<400> SEQUENCE: 94
ggagactctg agagaac                                                   17

<210> SEQ ID NO 95
<211> LENGTH: 14
<212> TYPE: DNA
<213> ORGANISM: Artificial Sequence
<220> FEATURE:
<223> OTHER INFORMATION: Probe 96 EV PR1

<400> SEQUENCE: 95 cgaggggag gatg                                                       14

<210> SEQ ID NO 96
<211> LENGTH: 16
<212> TYPE: DNA
<213> ORGANISM: Artificial Sequence
<220> FEATURE:

<223> OTHER INFORMATION: Probe HPV96

<400> SEQUENCE: 96
gaggctctga accagc                                                    16

<210> SEQ ID NO 97
<211> LENGTH: 21
<212> TYPE: DNA
<213> ORGANISM: Artificial Sequence
<220> FEATURE:
<223> OTHER INFORMATION: Probe UniEV PR1

<400> SEQUENCE: 97
tcttttttta caaggctttg g                                              21

<210> SEQ ID NO 98
<211> LENGTH: 21
<212> TYPE: DNA
<213> ORGANISM: Artificial Sequence
<220> FEATURE:
<223> OTHER INFORMATION: Probe UniEV PR2

<400> SEQUENCE: 98
tctttttttg aaaggctttg g                                              21

<210> SEQ ID NO 99
<211> LENGTH: 21
<212> TYPE: DNA
<213> ORGANISM: Artificial Sequence
<220> FEATURE:
<223> OTHER INFORMATION: Probe UniEV PR3

<400> SEQUENCE: 99
tcttttttta aaaggctttg g                                              21

<210> SEQ ID NO 100
<211> LENGTH: 21
<212> TYPE: DNA
<213> ORGANISM: Artificial Sequence
<220> FEATURE:
<223> OTHER INFORMATION: Probe UniEV PR4

<400> SEQUENCE: 100 tcttttcttta aaaggctttg g                                             21

<210> SEQ ID NO 101
<211> LENGTH: 23
<212> TYPE: DNA
<213> ORGANISM: Artificial Sequence
<220> FEATURE:
<223> OTHER INFORMATION: Probe UniEVPR1A

<400> SEQUENCE: 101
tcttttttta caaggctttg gac                                            23

<210> SEQ ID NO 102
<211> LENGTH: 23
<212> TYPE: DNA
<213> ORGANISM: Artificial Sequence
<220> FEATURE:
<223> OTHER INFORMATION: Probe UniEVPR1B

<400> SEQUENCE: 102
tcttttttta caaggctttg gaa                                            23

```
<210> SEQ ID NO 103
<211> LENGTH: 83
<212> TYPE: DNA
<213> ORGANISM: Human papillomavirus 5

<400> SEQUENCE: 103
tcttttttta caaggctttg gacacaatta gacctgagtg atcaagaaga ggagggcgag    60
gatggagaat ctcagcgagc gtt                                           83

<210> SEQ ID NO 104
<211> LENGTH: 83
<212> TYPE: DNA
<213> ORGANISM: Human papillomavirus 8

<400> SEQUENCE: 104
tctttttttg caaggctttg gacacaatta gagctgagtg atcaagaaga cgagggcgaa    60
catggagaat ctcagcgagc gtt                                           83

<210> SEQ ID NO 105
<211> LENGTH: 83
<212> TYPE: DNA
<213> ORGANISM: Human papillomavirus 9

<400> SEQUENCE: 105
tcttttttta aaaggctttg gacacagtta gatctgagtg atcaagaaga cgagggagag    60
gatggaaact ctcagcgcac gtt                                           83

<210> SEQ ID NO 106
<211> LENGTH: 83
<212> TYPE: DNA
<213> ORGANISM: Human papillomavirus 12

<400> SEQUENCE: 106 tcttttttg aaaggctttg gacacaatta gacctgagtg accaagaaga ggagggccaa    60
catggagaat ctcagcgagc gtt                                           83

<210> SEQ ID NO 107
<211> LENGTH: 83
<212> TYPE: DNA
<213> ORGANISM: Human papillomavirus 14

<400> SEQUENCE: 107
tctttcttta caaggctttg gaatcaatta gagctgagtg accaagaaga cgagggagac    60
aatggagaat ctcagcgacc gtt                                           83

<210> SEQ ID NO 108
<211> LENGTH: 83
<212> TYPE: DNA
<213> ORGANISM: Human papillomavirus 15

<400> SEQUENCE: 108
tctttttttg aaaggctttg gagacagtta gagctcagtg atcaagaaga cgagggagac    60
gatggatact ctcagcgaac gtt                                           83

<210> SEQ ID NO 109
<211> LENGTH: 83
<212> TYPE: DNA
<213> ORGANISM: Human papillomavirus 17

<400> SEQUENCE: 109
```

```
tcttttttg aaaggctttg gcatcagtta gatctgagtg atcaagaaga agagggagac      60
gatggacaat ctcagcgaac gtt                                           83
```

<210> SEQ ID NO 110
<211> LENGTH: 83
<212> TYPE: DNA
<213> ORGANISM: Human papillomavirus 19

<400> SEQUENCE: 110

```
tctttttta caaggctttg gcaacaatta gaactgagtg accacgaaga ggagggcgaa      60
aatggagaat ctcagcgaac gtt                                           83
```

<210> SEQ ID NO 111
<211> LENGTH: 83
<212> TYPE: DNA
<213> ORGANISM: Human papillomavirus 20

<400> SEQUENCE: 111

```
tctttttta caaggctttg gaagcaatta gagctgagtg accaagaaga cgagggagaa      60
aatggagaat ctcagcaagc gtt                                           83
```

<210> SEQ ID NO 112
<211> LENGTH: 83
<212> TYPE: DNA
<213> ORGANISM: Human papillomavirus 21

<400> SEQUENCE: 112

```
tctttttta caaggctttg gaatcaatta gagctgagtg accaagaaga cgagggagaa      60
aatggagaat ctcagcgatc gtt                                           83
```

<210> SEQ ID NO 113
<211> LENGTH: 83
<212> TYPE: DNA
<213> ORGANISM: Human papillomavirus 22

<400> SEQUENCE: 113

```
tctttttta aaaggctttg gacacaatta gaactgagtg atcaagaaga agagggagaa      60
aatggagaaa ctcagcgaac gtt                                           83
```

<210> SEQ ID NO 114
<211> LENGTH: 83
<212> TYPE: DNA
<213> ORGANISM: Human papillomavirus 23

<400> SEQUENCE: 114

```
tctttttta aaaggctttg gatacaatta ggactcagtg accaagagga cgagggagag      60
gatggaagca ctcagcgaac gtt                                           83
```

<210> SEQ ID NO 115
<211> LENGTH: 83
<212> TYPE: DNA
<213> ORGANISM: Human papillomavirus 24

<400> SEQUENCE: 115

```
tctttttta aaaggctttg gagacaatta gacctcagtg accaagaaga cgagggagag      60
gatggagaac ctgaaaaagc gtt                                           83
```

<210> SEQ ID NO 116
<211> LENGTH: 83

<212> TYPE: DNA
<213> ORGANISM: Human papillomavirus 25

<400> SEQUENCE: 116
tcttttttta caaggctttg gcatcaatta gacctgagtg accaagaaga cgagggcgaa    60
aatggagaat ctcagcgagc gtt                                           83

<210> SEQ ID NO 117
<211> LENGTH: 83
<212> TYPE: DNA
<213> ORGANISM: Human papillomavirus 36

<400> SEQUENCE: 117
tctttttttg aaaggctttg gacacaatta gaactcagtg accaagaaga cgagggcgaa    60
aatggagaat ctcagcgagc gtt                                           83

<210> SEQ ID NO 118
<211> LENGTH: 83
<212> TYPE: DNA
<213> ORGANISM: Human papillomavirus 37

<400> SEQUENCE: 118
tctttttttg aaaggctttg gaaacagtta gatctcagtg accaagaaga cgagggagac    60
gatggacaca ctcagcgatc gtt                                           83

<210> SEQ ID NO 119
<211> LENGTH: 83
<212> TYPE: DNA
<213> ORGANISM: Human papillomavirus 38

<400> SEQUENCE: 119
tctttcttta aaaggctctg gacacaatta gagctcagtg atcaagaaga cgagggagac    60
aatggaaact ctcagcgcac gtt                                           83

<210> SEQ ID NO 120
<211> LENGTH: 83
<212> TYPE: DNA
<213> ORGANISM: Human papillomavirus 47

<400> SEQUENCE: 120
tcttttttta caaggctttg gacacactta gacctgagtg accaagaaga cgagggcgaa    60
catggagaat ctcagcgagc gtt                                           83

<210> SEQ ID NO 121
<211> LENGTH: 83
<212> TYPE: DNA
<213> ORGANISM: Human papillomavirus 49

<400> SEQUENCE: 121
tctttttttg aaaggctttg gacacaatta gagctcagtg acccagaaga cgaggcagac    60
aatggaggca ctcaacgctc gtt                                           83

<210> SEQ ID NO 122
<211> LENGTH: 83
<212> TYPE: DNA
<213> ORGANISM: Human papillomavirus 75

<400> SEQUENCE: 122
tcttttttta aaaggctttg gagtcaatta gaactgagtg atcctgaaga cgaggcagac    60

```
aatggaggca ctcaacgatc gtt                                              83

<210> SEQ ID NO 123
<211> LENGTH: 83
<212> TYPE: DNA
<213> ORGANISM: Human papillomavirus 76

<400> SEQUENCE: 123 tctttttta aaaggctttg gaatcaatta gatctcagtg accctgaaga cgaggcagag        60
aatggaggca ctcaacgatc gtt                                              83

<210> SEQ ID NO 124
<211> LENGTH: 83
<212> TYPE: DNA
<213> ORGANISM: Human papillomavirus 80

<400> SEQUENCE: 124
tctttttttg aaaggctttg gagacagtta gatctcagtg atcacgaaga cgagggagac      60
gatggatact ctcagcgaac gtt                                              83

<210> SEQ ID NO 125
<211> LENGTH: 83
<212> TYPE: DNA
<213> ORGANISM: Human papillomavirus 92

<400> SEQUENCE: 125 tcttttttc aaaggctttg gggacaatta gatctaagtg accaagaaga cgagggtgag       60
gatggaggct ctcagcgacc gtt                                              83

<210> SEQ ID NO 126
<211> LENGTH: 83
<212> TYPE: DNA
<213> ORGANISM: Human papillomavirus 93

<400> SEQUENCE: 126 tctttttta caaggctttg gacacaatta gaactgagtg accaagaaga cgagggagag       60
gatggagact ctgagagaac gtt                                              83

<210> SEQ ID NO 127
<211> LENGTH: 83
<212> TYPE: DNA
<213> ORGANISM: Human papillomavirus 96

<400> SEQUENCE: 127 tcttttttc aaaggctttg gaagcagtta gatctaagtg accaagaaga cgaggggag        60 gatggaggct ctgaaccagc gtt                                              83
```

US 8,927,208 B2

IDENTIFICATION OF BETA-PAPILLOMAVIRUS DNA BY TYPE-SPECIFIC REVERSE HYBRIDIZATION

CROSS-REFERENCE TO RELATED APPLICATIONS

This application is the national phase of PCT application PCT/NL2006/000163 having an international filing date of 30 Mar. 2006, which claims priority from European Application No. 05075742.6 filed 30 Mar. 2005. The contents of the above applications are incorporated by reference herein in their entirety.

FIELD OF THE INVENTION

The present invention relates to the field of identification of beta-papillomavirus (beta-PV) infections.

BACKGROUND OF THE INVENTION

Papillomaviruses (PV) form a group of viruses associated with benign and malignant lesions of cutaneous and mucosal epithelia. So far, more than 100 different PV genotypes have been identified that infect humans. More than 30 of these human papillomavirus (HPV) types can be passed from person to person through sexual contact and are often called genital or mucosal HPVs. A further division of this group in low and high-risk types is made based on the association of the specific types with cervical cancer (1). Apart from these genital HPV types a second group of which approximately 48 types have been identified, exists that has a tropism for the cutaneous epithelia (2). These can be subdivided in classic wart types and the former B1 group, now designated as the beta-PV genus consisting of human PV (HPV) types 5, 8, 9, 12, 14, 15, 17, 19, 20, 21, 22, 23, 24, 25, 36, 37, 38, 47, 49, 75, 76, 80, HPVcand92, 93 and HPVcand96. Recently found partial PV sequences indicate however that more than 35 new types have probably to be added to the 25 already known beta-PV types (3).

Originally, members of this genus have been found in skin lesions from patients with the rare hereditary disease epidermodysplasia verruciformis (EV). The disorder is characterized by numerous flat cutaneous warts, and a high-risk of cutaneous squamous cell carcinomas (SCCs) mostly localized on the sun-exposed areas of the skin. In contrast to the presence of multiple HPV types in the benign lesions, mostly HPV types 5 and 8 and sometimes HPV types 14, 17, 20 or 47 have been detected in the SCCs of EV-patients, which may be regarded as high-risk types (3).

HPV DNA detection, mainly by nested PCR, identified DNA from beta-PV types in 30-50% of SCCs in immunocompetent patients and in up to 80% of the SCCs in immunosuppressed patients, e.g. renal transplant recipients (4). These epidemiological studies based on HPV DNA detection delivered at the present no convincing evidence for the existence of high-risk beta-PV types analogous to the high-risk genital HPV types (5). This may be (partially) due to the frequently used nested PCR, since its sensitivity is not known for most individual types but probably varies with regard to individual types by several orders of magnitude. Misclassification by sequence analysis of the amplimers of the former MaHa PCR (5), especially when multiple types are present in lesions or plucked hairs, may also underlie this observation. Also the power of the epidemiological studies that were carried out until now may play a role.

Only little knowledge is available on the biological properties of the beta-PV types. As a result no more than speculations about the mechanism of beta-PV related carcinogenesis are possible. In contrast to cervical cancer, skin cancer related to HPV is probably caused by an interaction between beta-PV types and ultraviolet radiation. The early viral protein E6 of some types of beta-PV may impair the DNA repair process and prevent apoptosis after exposure to ultraviolet radiation (6, 7, and 8). As a result, beta-PV-infected, DNA-damaged cells may survive. This may ultimately lead to cutaneous (pre)malignant lesions like actinic keratoses and SCCs.

Establishing an association between one or more specific beta-PV types and premalignant and malignant lesions like solar keratoses and SCCs requires very large epidemiologic case-control and cohort studies involving the detection and genotyping of HPV DNA in a large number of samples, often containing multiple beta-PV types.

Several PCR-primer sets have already been developed to detect beta-PV types in skin biopsies, plucked hairs and skin swabs. Until now beta-PV genotyping is performed either by sequencing of broad spectrum PCR amplimers or by as type-specific PCRs. However, when typing of all the 25 known beta PV types is required in a large epidemiological study, a faster and more reliable method is required. Earlier experiences with the established SPF10-LiPA system show that a reverse hybridisation assay is well suited for this purpose (9).

SUMMARY OF INVENTION

The present invention relates to a method for typing of any beta-PV nucleic acid possibly present in a sample, the method comprising the steps of contacting any such nucleic acid with at least one probe capable of specific hybridization within the A region of beta-PV, said region being indicated in FIG. 1, and then analysing beta-PV type(s) based upon the hybridisation result so obtained.

The invention further relates to a method for typing of any beta-PV nucleic acid possibly present in a biological sample, the method comprising a step to detect the presence of beta-PV nucleic acid present in a sample prior to or simultaneously with any typing step.

The invention further relates to oligonucleotide probes enabling said method of identification, of beta-PV.

The invention further relates to protocols according to which said hybridization steps can be performed. One format for the hybridization step is, for instance, the reverse hybridization format.

The invention further relates to kits comprising probes and/or instructions for use in carrying out the invention.

FIGURES

FIG. 1 illustrates an alignment of different beta-PV sequences (SEQ ID NOS:104-127) with reference to the sequence of an HPV 5 sequence (SEQ ID NO:103) Genbank accession number M17463, and showing location of the A and B regions.

FIG. 4 illustrates the outline of the skin (beta) HPV genotyping strip.

Figure 2:
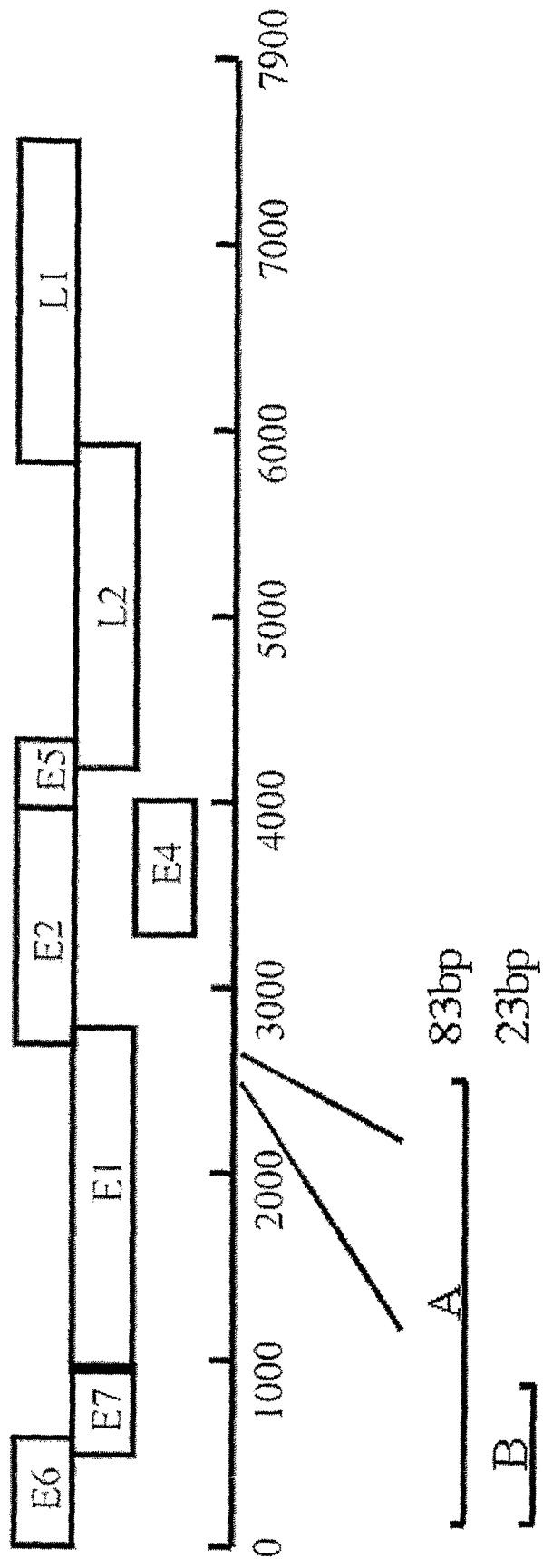
FIG. 2 illustrates the outline of the HPV genome. Relative to the position on the HPV genome the HPV genes and the A and B regions are depicted.

A possible make-up for the strip that enables detection and identification of 25 beta-PV genotypes is shown. The lines correspond to the positions of the probes and the names of the probes are from Table 1. "Universal" indicates the position where the 4 universal probes are applied (Table 2). Biotinylated poly(dT)40 serves as a positive control for the conjugate and substrate reaction and is designated as "Conjugate control".

FIG. 5 illustrates the typical patterns arising upon analysis of amplimers with the skin (beta) HPV genotyping strip. The amplimers were obtained by performing PCR on plasmid clones of 23 beta-PV genotypes and 2 beta candPV genotypes (genotyping results representing HPV types 5, 8, 9, 12, 14, 15, 17, 19-25, 36-38, 47, 49, 75, 76, 80, 92, 93, and 96 are shown from respectively strip 1 to 25).

DETAILED DESCRIPTION

The present invention generally relates to a method for typing of any beta-PV nucleic acid possibly present in a biological sample, the method comprising the steps of contacting any such nucleic acid present with at least one probe capable of specific hybridization within the A region of the beta-PV genome, said A region being indicated in FIG. 1, and then detecting any specific hybridization that might result to determine if there is beta-PV nucleic acid in the sample, and to which beta-PV type it might belong.

Preferably the probe is capable of specific hybridisation within the A region of the HPV genome.

We have determined that the 83 nucleotides A region of the HPV genome (see FIG. 1) is highly informative in respect of beta-PV typing.

The method of the invention thus generally comprises hybridization of nucleic acid from beta-PV with a probe capable of hybridizing to the A region of beta-PV, said hybridization event, or even absence of a hybridisation event, providing information which allows different beta-PV types to be discriminated.

The hybridisation of probe with target nucleic acid takes place under reaction conditions where specific hybridisation of the probe can occur.

The analysis of beta-PV type(s) present in the sample may be carried out at different levels of resolution.

Analysis may be at a resolution suitable to identify individual beta-PV types, such as beta-PV 5, 8 or 23, for example.

Whilst the typing assay of the present invention is suitably able to provide information on all specific types found in a sample, nevertheless it may not be necessary (from the point of view of the user) to be able to discriminate between exact beta-PV types, and the output of the assay may only need to be at the level of categories of beta-PV types.

The invention thus relates to a method of HPV typing, the method also allowing the identification of high risk HPV types, without indication of which specific high risk type is present in a sample.

The category of possible high-risk types, those found in Squamous Cell Carcinomas (SCCs), includes e.g., HPV 5 and 8. This has been acknowledged by a study of the WHO Monograph working group (Cogliano, V. et al., Oncology, The Lancet. Vol. 6, April 2005). The Working Group concluded that human papillomavirus types 16, 18, 31, 33, 35, 39, 45, 51, 52, 56, 58, 59, and 66 are carcinogenic to human beings. Human papillomaviruses 6, 11, and that some human papillomavirus types of the genus beta (including types 5 and 8) are possibly carcinogenic to human beings.

Preferably the specific probes used in the invention are capable of specific hybridisation within the 83 nucleotide "A" region of the beta-PV genome, where this region is given by reference to the sequence of FIG. 1. These regions correspond to nucleotides 2662-2744 (A region) of the HPV 5 reference sequence M17463.

It will be appreciated that reference to A region using the numbering of FIG. 1 herein includes equivalent regions in other beta-PV sequences which are not specifically listed, and which may vary from the beta-PV reference sequence or other sequences given. An equivalent A and B region in a yet unknown beta-PV genome may be identified on the basis of, for example, sequence homology or identity with the sequences of FIG. 1.

Sequence comparisons of nucleic acid identity/homology are readily carried out by the skilled person, for example using the BLAST and BLAST 2.0 algorithms, which are described by Altschul and coworkers (10, 11). BLAST and BLAST 2.0 can be used, for example with the default parameters, to determine percent sequence identity for the polynucleotides of the invention. Software for performing BLAST analyses is publicly available through the National Center for Biotechnology Information.

Thus the invention can be seen to relate to probes and to the use of probes which are capable of specific hybridization within the A region of HPV, said region being indicated in FIG. 1 or which are capable of specific hybridization within an equivalent region in another HPV genome, the equivalent region being assessed by nucleic acid identity and/or homology.

The present invention also relates to nucleic acid fragments consisting essentially of the isolated 83 base pair A region, either region being in single or double stranded nucleic acid form, as RNA or DNA, and to use of these nucleic acid fragments regions in typing of beta-PV.

One feature of the present invention is the selection of suitable probes.

Probes which specifically hybridise to preferred A region of the beta-PV genome are preferably able to provide information (via hybridisation results) as to the type of the beta-PV strain present, either alone or in combination with information from another probe or probes. Information about beta-PV type is preferably obtained by positive detection of hybridisation of a probe with target nucleic acid, but may also be obtained by absence of hybridisation of a given probe.

Suitably a probe of the present invention is capable of specific hybridization within the A region of the genome of only one beta-PV type, and thus enables specific identification of this beta-PV type, when this type is present in a biological sample.

Thus an embodiment of the invention relates to a method for typing of any beta-PV nucleic acid possibly present in a biological sample, the method comprising the steps of contacting any such nucleic acid with at least one probe capable of specific hybridization within the A region, of the genome of only one beta-PV type, said regions being indicated in FIG. 1, and then analysing beta-PV type(s) based upon the hybridisation result so obtained.

A probe of the present invention may still provide useful information if it is capable of specific hybridization within the A region of the genome of a limited number of types, such as only 2 HPV types. For example this can enable identification of these types, or may enable specific identification of each type in combination with information from another probe.

Probes capable of giving information about beta-PV types, such as those above, are generally considered as type specific probes herein. According to the invention, these type specific probes are capable of specific hybridization within the A region, of the genome of only one beta-PV type (FIG. 1).

The different types of beta-PV in a sample can be identified by hybridization of nucleic acids of said types of beta-PV to at least one, preferably at least two, more preferably at least three, even more preferably at least four and most preferably at least five oligonucleotide probes.

Table 1 contains a list of preferred probes specifically hybridizing to the A region. These probes may be used together, suitably under the same conditions of hybridization and washing. Preferred is a reverse hybridization format, such as a line probe assay format for example. All probes listed are herein individually claimed. Moreover, all combinations of probes are herein contemplated.

The probes listed in Table 1 specifically hybridise to the A region of specific beta-PVs and thus are able to provide information about specific types of beta-PV target nucleic acid that may be present in a sample.

It will be clear to one skilled in the art that probes other than those listed in Table 1 may be chosen within said A, preferably probes that specifically hybridize to only one beta-PV type and/or which are capable of providing information allowing beta-PV type determination.

Probes for use in the present invention may have an additional spacer sequence which does not form part of the probe itself but which can allow for attachment to a solid support, for example. The spacer region may be added enzymatically or chemically and may be 5' or 3' of the probe.

Suitably the use of probes of the invention allow typing of at least 5 different beta-PV types, preferably at least 10 different beta-HPV types, more preferably at least 5, 8, 9, 12, 14, 15, 17, 19, 20, 21, 22, 23, 24, 25, 36, 37, 38, 47, 49, 75, 76, 80, HPVcand92, 93 and HPVcand96. Most preferably the present invention allows more than 25 different beta-HPV types to be differentiated, suitably more than 30.

Figure 3:
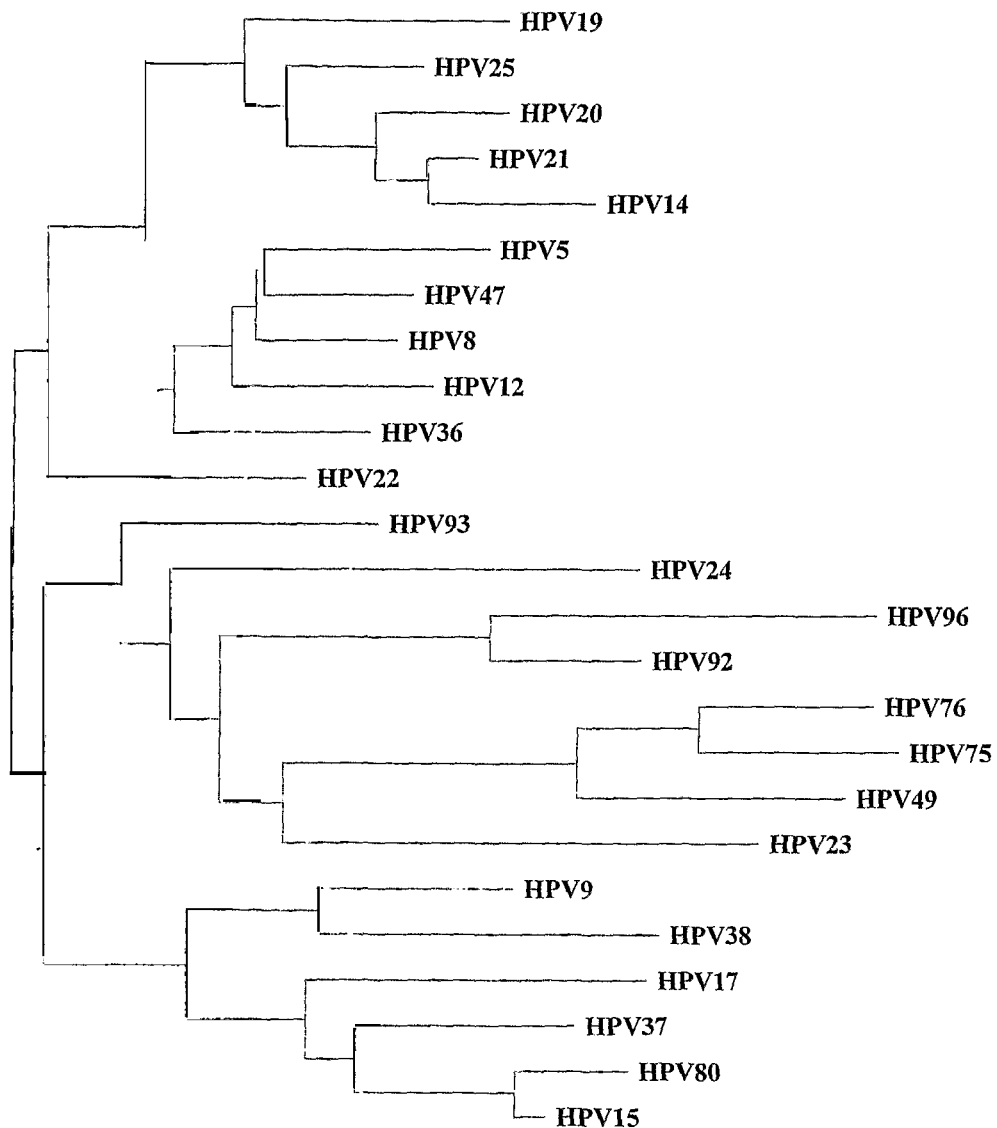
FIG. 3 illustrates the phylogenetic tree of region A from 25 beta-PV genotypes.

Suitably all of the beta-PV types given in the phylogenetic tree of FIG. 3, or substantially all, can be differentiated using the invention outlined herein.

Any beta-PV nucleic acid present in the sample may optionally first be amplified, for example by PGR or other suitable amplification process, prior to hybridization. Amplification of any target nucleic acid may be carried out using so called "broad spectrum" primers or primer sets that allow for amplification of all beta-PV nucleic acid in a sample, regardless of type.

Reference to beta-PV nucleic acid present in a sample thus includes nucleic acid that has been amplified from a sample, where this is clear from the context (i.e. an amplification step is present prior to hybridization).

Thus, in one embodiment the present invention relates to a method for typing of any beta-PV nucleic acid possibly present in a biological sample, the method comprising the steps of:
(i) contacting any nucleic acid fragments with at least one probe capable of specific hybridization with the A region of beta-PV said A region being indicated in FIG. 1.

In another aspect of the invention the probes disclosed in the present invention may also be used in quantitative PCR protocols or quantitative hybridisation protocols. Quantitative PCR (QPCR) allows quantification of starting amounts of DNA, cDNA, or RNA templates. QPCR can be based on the detection of a fluorescent reporter molecule that increases as PCR product accumulates with each cycle of amplification. Fluorescent reporter molecules include dyes that bind double-stranded DNA (i.e. SYBR Green I) or sequence-specific probes (i.e. Molecular Beacons or TaqMan® Probes).

As discussed above certain probes may provide information about the exact beta-PV type, for example if they are able to hybridise to a given type but not to other types (i.e., type specific probes). Probes that are specific for the A region or B region may also be used to more generally determine if there is any beta-PV nucleic acid present in a sample without necessarily giving typing information. Such probes may be referred to as 'universal beta-PV probes' herein. Table 2 listed preferred universal probes. Samples which are found to be positive for beta-PV nucleic acid can then be specifically typed using specific typing methods, such as type specific probes or type specific PCR. Alternatively samples can be both probed with universal probes and specifically typed simultaneously.

Universal probes may contain inosine residues as part of the nucleic acid probe sequence, which allows for some flexibility in hybridisation to target nucleic acid, and can allow hybridisation to the A or B region of different beta-PV types.

For the avoidance of doubt, probes that specifically hybridise to the A region of any beta-PV nucleic acid in a sample may be universal (if that they hybridise to multiple HPV types in the A region and/or do not give specific typing information) or type-specific probes which identify one specific beta-PV. It is possible that both universal and specific probes recognise an unknown beta-PV nucleic acid to be typed.

Where the target DNA is amplified prior to typing, universal probes which fall within the preferred A or B regions may also be used to detect beta-PV nucleic acid.

The invention thus also relates to probes, or groups of probes, which are able to identify the presence of any beta-PV nucleic acid in a sample.

Universal probes may be used to detect beta-PV nucleic acid e.g., using the DNA Enzyme Immuno Assay (DEIA) technique, for example as referred to in WO991437 and described for example by Zella and coworkers (12). This method is used for rapid and specific detection of PCR products. PCR products are generated by a primer set, of which both the forward and the reverse primer contain biotin at the 5' end. This allows binding of the biotinylated amplimers to streptavidin-coated microtiter wells. PCR products are denatured by sodium hydroxide. Specific labelled oligonucleotide probes (e.g. with digoxigenin) are hybridized to the single stranded immobilized PCR product and hybrids are detected by enzyme-labelled conjugate and colorimetric or fluorimetric methods.

In the present invention there are provided a group of universal probes suitable for determination of the presence of beta-PV nucleic acid in a sample, suitably in the DEIA technique. Suitably such probes can be used under the same reaction conditions. Preferred probes are given in Table 2. All probes described therein are claimed individually, and in combination. The invention suitably provides a combination of any 2 probes of Table 2, suitably any 3, and 4, and 5 or more probes for general detection of beta-PV (i.e., detection of any HPV type), preferably all probes included in Table 2.

A separate embodiment the invention relates to use of universal probes that specifically hybridise within the A or B region of the beta-PV genome, such as those of Table 2, in combination with a subsequent or simultaneous typing step.

After the hybridization between the probe and any target DNA, detection of the hybridization may be carried out by any suitable means. For example, the probe and/or nucleic acid target may be detectably labelled. To assist in detection it is preferred that the target and/or the signal are amplified. PCR amplification of the target DNA is especially preferred.

The hybridisation between probe and target is preferably carried out in the presence of a solid support, although this is not obligatory. One or more of the probe and target nucleic acid may be immobilised, for example, being fixed to a beads, plates, slide or a microtitre dish. Alternatively neither probe nor target may be immobilised. Hybridisation may be carried out in the context of a liquid medium.

Detection of binding maybe carried out using flow cytometry, for example using the Luminex™ flow cytometry system (see, for example, WO9714028 and http://www.luminex-corp.com/).

Detection of binding may also be carried out in the context of a microarray, using for example methods as described in EP373203, EP386229, EP0804731 and EP619321 and incorporated herein by reference. Such techniques are well known to the person skilled in the art.

According to another preferred embodiment of the present invention, the aforementioned methods of identification of beta-PV are characterized further in that the hybridization step involves a reverse hybridization format. In one embodiment the probes are immobilized to certain locations on a solid support. In another embodiment the probes are hybridised to beads, in which case they do not adopt a fixed position relative to one another.

Suitably any beta-PV nucleic acid in a sample is amplified as described above, and the amplified beta-PV polynucleic acids are labelled in order to enable the detection of the hybrids formed.

According to this embodiment, at least one probe, or a set of a least 2, preferably at least 3, more preferably at least 4 and most preferably at least 5 probes is used. When at least 2 probes are used, said probes are designed in such a way that they specifically hybridize to their target sequences under the same hybridization conditions and the same wash conditions.

In preferred reverse hybridization assays the oligonucleotide probes are immobilized on a solid support as parallel lines (13; international application WO 94/12670). The reverse hybridization format has many practical advantages as compared to other DNA techniques or hybridization formats, especially when the use of a combination of probes is preferable or unavoidable to obtain the relevant information sought.

Optionally, where required, typing methods of the present invention include a type specific PCR step after the hybridization step, for example as disclosed in WO03014402, incorporated herein by reference. Type specific PCR is designed to amplify a specific beta-PV nucleic acid type, for example HPV 5 DNA only, as compared with non specific primers which may be used prior to beta-PV typing and generally serve to amplify nucleic acid form multiple beta-PV types.

The present invention also relates to type specific primers that are capable of amplification of HPV nucleic acid comprising the A region of the beta-PV genome.

In another embodiment the invention thus relates to a method comprising:
1 Typing of the beta-PV nucleic acid in samples in which beta-PV nucleic acid has been detected by contacting such nucleic acid with at least one probe capable of specific hybridization within the A region, suitably within the B region, of beta-PV, said regions being indicated in FIG. 1, and then analysing beta-PV type based upon the hybridisation result so obtained, and
2 Optionally, amplification and detection of any nucleic acid in a sample using type specific primers for types not identified in step 1.

The present invention also relates to kits for use in the present invention, to detect and/or identify beta-PV types.

A kit can comprise at least 2 probes capable of specific hybridization to fragment 2662-2744 of the beta-PV genome, with numbering given in respect of FIG. 1. Preferred probes are capable of allowing discrimination between different beta-PV types, with suitable probes listed in Table 1.

A kit can comprise instructions for carrying out the above methods for beta-PV identification and typing analysis, in combination with a probe as indicated above.

A kit can comprise at least one probe, as given above.

A kit can comprise a probe of the present invention immobilised onto a solid support. The support can be a bead, microtitre plate or slide, for example.

A kit can comprise a universal probe or probes, suitably a probe or probes given in Table 2.

The present invention also relates to diagnostic kits for identification of beta-PV possibly present in a biological sample, comprising the following components: (i) at least one suitable probe, preferably at least 2, more preferably at least 3, even more preferably at least 4 and most preferably at least 5 suitable probes, optionally fixed to a solid support.

Suitably a kit additionally comprises one or more of the following:
(ii) a hybridization buffer, or components necessary for the production of said buffer, or instructions to prepare said buffer;
(iii) a wash solution, or components necessary for the production of said solution, or instructions to prepare said solution;
(iv) a means for detection of the hybrids formed;
(v) a means for attaching the probe(s) to a known location on a solid support.

The following definitions and explanations will permit a better understanding of the present invention.

HPV isolates (like beta-PV) that display a sequence difference of more than 10% to any previously known type in a 291 bp fragment from the L1 region (14) are classified as different HPV "types". HPV isolates that differ between 2 and 10% are classified as different "subtypes". If the sequence variation is below 2%, the isolates are classified within the same subtype as different "variants". The term "type" when applied to HPV refers to any of the three categories defined above.

The target material in the samples to be analyzed may either be DNA or RNA, e.g. genomic DNA, messenger RNA, viral RNA or amplified versions thereof. These molecules are in this application also termed "nucleic acids" or "polynucleic acids".

Well-known extraction and purification procedures are available for the isolation of RNA or DNA from a sample (e.g. described in reference 15).

The term "probe" according to the present invention generally refers to a single-stranded oligonucleotide which is designed to specifically hybridize to beta-PV polynucleic acids.

The term "primer" generally refers to a single stranded oligonucleotide sequence capable of acting as a point of initiation for synthesis of a primer extension product which is complementary to the nucleic acid strand to be copied. The length and the sequence of the primer must be such that they allow to prime the synthesis of the extension products.

Preferably the primer is about 10-50 nucleotides long. Specific length and sequence will depend on the complexity of the required DNA or RNA targets, as well as on the conditions at which the primer is used, such as temperature and ionic strength.

The expression "primer pair" or "suitable primer pair" in this invention refers to a pair of primers allowing the amplification of part or all of the beta-PV polynucleic acid fragment for which probes are able to bind.

The term "target" or "target sequence" of a probe according to the present invention is a sequence within the beta-PV polynucleic acids to which the probe is completely complementary or partially complementary (where partially complementary allows for some degree of mismatch). It is to be understood that the complement of said target sequence is also a suitable target sequence in some cases. Probes of the present invention are suitably complementary to at least the central part of their target sequence. In most cases the probes are completely complementary to their target sequence. The term "type-specific target sequence" refers to a target sequence within the polynucleic acids of a given beta-PV type that contains at least one nucleotide difference as compared to any other beta-PV-type.

"Specific hybridization" to a region of the beta-PV polynucleic acids means that said probe forms a duplex with part of this region or with the entire region under the experimental conditions used, and that under those conditions said probe does not form a duplex with other regions of the polynucleic acids present in the sample to be analysed. It should be understood that probes that are designed for specific hybridisation within a region of beta-PV polynucleic acid may fall entirely within said region or may to a large extent overlap with said region (i.e. form a duplex with nucleotides outside as well as within said region).

Suitably the specific hybridisation of a probe to a nucleic acid target region occurs under stringent hybridisation conditions, such as 3×SSC, 0.1% SDS, at 50° C.

The skilled person knows how to vary the parameters of temperature, probe length and salt concentration such that specific hybridisation can be achieved. Hybridization and wash conditions are well known (exemplified in reference 15, particularly Chapter 11 therein). When needed, slight modifications of the probes in length or in sequence can be carried out to maintain the specificity and sensitivity required under the given circumstances. Probes and/or primers listed herein may be extended by 1, 2, 3, 4 or 5 nucleotides, for example, in either direction (upstream or downstream of region A).

Preferred stringent conditions are suitably those which allow for a type specific probe binding to only one beta-PV type. These conditions are known from e.g. Maniatis et al., Cold Spring Harbor and Ausubel et al. "A LABORATORY MANUAL", Cold Spring Harbor Laboratory (1988). Thus in an embodiment of the invention the method for typing of any beta-PV nucleic acid possibly present in a biological sample comprises the steps of contacting any such nucleic acid with at least one probe which is capable of hybridisation to the A region of beta-PV under stringent conditions.

Specific hybridization of a primer to a region of the beta-PV polynucleic acids means that, during the amplification step, said primer forms a duplex with part of this region or with the entire region under the experimental conditions used, and that under those conditions said primer does not form a duplex with other regions of the polynucleic acids present in the sample to be analysed. It should be understood that primers that are designed for specific hybridization to a region of beta-PV polynucleic acids, may fall within said region or may to a large extent overlap with said region (i.e. form a duplex with nucleotides outside as well as within said region). Hybridization can occur between DNA-DNA, between DNA-RNA and between RNA-RNA nucleotide sequences.

Suitably each nucleotide of the probe can form a hydrogen bond with its counterpart target nucleotide.

Preferably the complementarity of probe with target is assessed by the degree of A:T and C:G base pairing, such that an adenine nucleotide pairs with a thymine, and such that a guanine nucleotide pairs with a cytosine, or vice versa. In the RNA form, T may be replaced by U (uracil).

Probes which specifically hybridise to the A region of the beta-PV genome as defined herein suitably at least 95% complementary to the target sequence over their length, suitably greater than 95% identical such as 96%, 97%, 98%, 99% and most preferably 100% complementary over their length to the target beta-PV sequence. The probes of the invention can be complementary to their target sequence at all nucleotide positions, with 1, 2, or more mismatches possibly tolerated depending upon the length of probe, temperature, reaction conditions and requirements of the assay, for example.

Where inosine is used in universal probes, for example, or in primers, then complementarity may also be assessed by the degree of inosine (probe)-target nucleotide interactions.

As such, the present invention can also be seen to relate to a method for detection and/or typing of any beta-PV nucleic acid possibly present in a biological sample, the method comprising the steps of contacting any such nucleic acid with at least one probe, the probe having 1, or 0 nucleotide mismatches across its length to the A region, of an beta-PV genome, said regions being indicated in FIG. 1, and then analysing beta-PV type based upon the hybridisation result so obtained.

An embodiment of the present invention requires the detection of single base pair mismatches and stringent conditions for hybridization of probes are preferred, allowing only hybridization of exactly complementary sequences. However, it should be noted that, since the central part of the probe is essential for its hybridization characteristics, possible deviations of the probe sequence versus the target sequence may be allowable towards the extremities of the probe when longer probe sequences are used. Variations are possible in the length of the probes.

Said deviations and variations, which may be conceived from the common knowledge in the art, should however always be evaluated experimentally, in order to check if they result in equivalent hybridization characteristics as the exactly complementary probes.

Preferably, the probes of the invention are about 5 to 50 nucleotides long, more preferably from about 10 to 25 nucleotides. Particularly preferred lengths of probes include 5, 6, 7, 8, 9, 10, 11, 12, 13, 14, 15, 16, 17, 18, 19, 20, 21, 22, 23, 24 or 25 nucleotides (without counting any spacer sequences that may be present). The nucleotides as used in the present invention may be ribonucleotides, deoxyribonucleotides and modified nucleotides such as inosine or nucleotides containing modified groups which do not essentially alter their hybridization characteristics. This is similar to the method described in US2003/165821.

Probe sequences are represented throughout the specification as single stranded DNA oligonucleotides from the 5' to the 3' end. It is obvious to the person skilled in the art that any of the below-specified probes can be used as such, or in their complementary form, or in their RNA form (wherein T is replaced by U).

The probes according to the invention can be prepared by cloning of recombinant plasmids containing inserts including the corresponding nucleotide sequences, if need be by excision of the latter from the cloned plasmids by use of the adequate nucleases and recovering them, e.g. by fractionation according to molecular weight. The probes according to the present invention can also be synthesized chemically, for instance by the conventional phospho-triester method.

Primers may be labelled with a label of choice (e.g. biotin). The amplification method used can be either polymerase chain reaction (PCR) (16), ligase chain reaction (LCR) (17, 18), nucleic acid sequence-based amplification (NASBA) (19, 20), transcription-based amplification system (TAS) (21), strand displacement amplification (SDA) (22) or amplification by means of QB replicase (23) or any other suitable method to amplify nucleic acid molecules known in the art.

The oligonucleotides used as primers or probes may also comprise nucleotide analogues such as phosphorothiates (24), alkylphosphorothiates or peptide nucleic acids (25) or may contain intercalating agents (26). As most other variations or modifications introduced into the original DNA sequences of the invention these variations will necessitate adaptions with respect to the conditions under which the oligonucleotide should be used to obtain the required specificity and sensitivity. However the eventual results of hybridization will be essentially the same as those obtained with the unmodified oligonucleotides. The introduction of these modifications may be advantageous in order to positively influence characteristics such as hybridization kinetics, reversibility of the hybrid-formation, biological stability of the oligonucleotide molecules, etc.

The term "solid support" can refer to any substrate to which an oligonucleotide probe can be coupled, provided that it retains its hybridization characteristics and provided that the background level of hybridization remains low. Usually the solid substrate will be a microtiter plate (e.g. in the DEIA technique), a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, NH2 groups, SH groups, carboxylic groups, or coupling with biotin, haptens or proteins.

As discussed above, hybridisation may take place in liquid media, and binding of probe to target assessed by, for example, flow cytometry.

The term "labelled" generally refers to the use of labelled nucleic acids. Labelling may be carried out by the use of labelled nucleotides incorporated during the polymerase step of the amplification such as illustrated by Saiki and coworkers (16) or Bej and coworkers (27, 28) or labelled primers, or by any other method known to the person skilled in the art. The nature of the label may be isotopic ("P, "S, etc.) or non-isotopic (biotin, digoxigenin, etc.).

The "sample" may be any material which may contain HPV nucleic acid, such as biological material, for example taken either directly from a human being (or animal), or after culturing (enrichment), or may be recombinant HPV nucleic acid expressed in a host cell. Biological material may be e.g. urine, or scrapes/biopsies from the skin, or exposed tissue in wounds, or any part of the human or animal body, such as the urogenital tract.

The sets of probes of the present invention will generally include at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more probes.

Said probes may be applied in two or more (possibly as many as there are probes) distinct and known positions on a solid substrate. Often it is preferable to apply two or more probes together in one and the same position of said solid support. The invention relates to a solid support having 1 or more probes of the present invention attached to it.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions are explained further herein.

The stability of the [probe: target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be more stable at higher temperatures.

Conditions such as ionic strength and incubation temperature under which a probe will be used should also be taken into account when designing a probe. It is known that the degree of hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

The length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly complementary base sequence will normally primarily determine hybrid stability.

While oligonucleotide probes of different lengths and base composition may be used, preferred oligonucleotide probes of this invention are between about 5 to 50 (more particularly 10-25) bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided.

It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are > available to search for this type of interaction. However, in certain instances, it may not be possible to avoid this type of interaction.

In order to identify different beta-PV types with the selected set of oligonucleotide probes, any hybridization method known in the art can be used (conventional dot-blot, Southern blot, sandwich, etc.). However, in order to obtain fast and easy results if a multitude of probes are involved, a reverse hybridization format may be most convenient. In a preferred embodiment the selected probes are immobilized to a solid support in known distinct locations (dots, lines or other Figures). In another preferred embodiment the selected set of probes are immobilized to a membrane strip in a line fashion. Said probes may be immobilized individually or as mixtures to delineated locations on the solid support. A specific and very user-friendly embodiment of the above-mentioned preferential method is disclosed in Example 4 of WO9914377, which may be adapted in the present invention. The beta-PV polynuceleic acids can be labelled with biotin, and the hybrid can then, via a biotine-streptavidine coupling, be detected with a non-radioactive colour developing system.

The term "hybridization buffer" means a buffer allowing a hybridization reaction between the probes and the poly-nucleic acids present in the sample, or the amplified products, under the appropriate stringency conditions.

The term "wash solution" means a solution enabling washing of the hybrids formed under the appropriate stringency conditions.

Throughout this specification and the claims which follow, unless the context requires otherwise, the word "comprise", and variations such as "comprises" and "comprising", will be understood to imply the inclusion of a stated integer or step or group of stated integers or steps but not to the exclusion of any other integer or step or group of integers or steps. 'Comprising' also implies the inclusion of the meanings, 'consisting of' and 'consisting essentially of'.

REFERENCES

1. Munoz N, Bosch F X, de Sanjose S, Herrero R, Castellsague X, Shah K V, Snijders P J, Meijer C J. Epidemiologic classification of human papillomavirus types associated with cervical cancer. N Engl J Med. 2003 Feb. 6; 348(6): 518-27
2. de Villiers E M, Fauquet C, Broker T R, Bernard H U, zur Hausen H. Classification of papillomaviruses. Virology. 2004 Jun. 20; 324(1): 17-27
3 Pfister H. Chapter 8: Human papillomavirus and skin cancer. J Natl Cancer Inst Monogr. 2003; (31):52-6
4. de Jong-Tieben L M, Berkhout R J, Smits H L, Bouwes Bavinck J N, Vermeer B J, van der Woude F J, ter Schegget J. High frequency of detection of epidermodysplasia verruciformis-associated human papillomavirus DNA in biopsies from malignant and premalignant skin lesions from renal transplant recipients. J Invest Dermatol. 1995 September; 105(3):367-71
5. Berkhout R J, Bouwes Bavinck J N, ter Schegget J. Persistence of human papillomavirus DNA in benign and (pre) malignant skin lesions from renal transplant recipients. J Clin Microbiol. 2000 June; 38(6):2087-96
6. Iftner T, Elbel M, Schopp B, Hiller T, Loizou J I, Caldecott K W, Stubenrauch F. Interference of papillomavirus E6 protein with single-strand break repair by interaction with XRCC1. EMBO J. 2002 Sep. 2; 21(17):4741-8
7. Jackson S, Storey A. E6 proteins from diverse cutaneous HPV types inhibit apoptosis in response to UV damage. Oncogene. 2000 Jan. 27:19(4):592-8
8. Giampieri S, Storey A. Repair of UV-induced thymine dimers is compromised in cells expressing the E6 protein from human papillomaviruses types 5 and 18. Br J Cancer. 2004 Jun. 1; 90(11):2203-9
9. Kleter B, van Doom L J, Schrauwen L, Molijn A, Sastrowijoto S, ter Schegget J, Lindeman J, ter Harmsel B, Burger M, Quint W. Development and clinical evaluation of a highly sensitive PCR-reverse hybridization line probe assay for detection and identification of anogenital human papillomavirus. J Clin Microbiol. 1999 August; 37(8):2508-17
10. Altschul S F, Madden T L, Schäffer A A, Zhang J, Zhang Z, Miller W, and Lipman D J Gapped BLAST and PSI-BLAST: a new generation of protein database search programs. Nucleic Acids Res. 1997 Sep. 1; 25(17): 3389-3402
11. Altschul S F, Gish W, Miller W, Myers E W, Lipman D J. Basic local alignment search tool. J Mol Biol. 1990 Oct. 5; 215(3):403-10
12. Zella D, Cavicchini A, Cattaneo E, Cimarelli A, Bertazzoni U. Utilization of a DNA enzyme immunoassay for the detection of proviral DNA of human immunodeficiency virus type 1 by polymerase chain reaction. Clin Diagn Virol. 1995 February; 3(2):155-64
13. Stuyver L, Rossau R, Wyseur A, Duhamel M, Vanderborght B, Van Heuverswyn H, Maertens G. Typing of hepatitis C virus isolates and characterization of new subtypes using a line probe assay. J Gen Virol. 1993 June; 74 (Pt 6):1093-102
14. Chan S Y, Delius H, Halpern A L, Bernard H U. Analysis of genomic sequences of 95 papillomavirus types: uniting typing, phylogeny, and taxonomy. J Virol. 1995 May; 69(5):3074-83
15. Sambrook et al. 1989 Molecular Cloning: A Laboratory Manual, 2nd Edition, Cold Spring Harbour Laboratory Press
16. Saiki R K, Gelfand D H, Stoffel S, Scharf S J, Higuchi R, Horn G T, Mullis K B, Erlich H A Primer-directed enzymatic amplification of DNA with a thermostable DNA polymerase. Science 1988, 29; 239(4839):487-491
17. Wu D Y, Wallace R B The ligation amplification reaction (LAR)-amplification of specific DNA sequences using sequential rounds of template-dependent ligation. Genomics 1989, 4(4):560-569
18. Bar any F The ligase chain reaction on a PGR world, PCR Methods Appl. 1991, 1(1):5-16 Erratum in: PCR Methods Appl. 1991, 1(2):149
19. Guatelli J C, Whitfield K M, Kwoh D Y, Barringer K J, Richman D D, Gingeras T R. Isothermal, in vitro amplification of nucleic acids by a multienzyme reaction modelled after retroviral replication. Proc Natl Acad Sci USA 1990, 87(5): 1874-1878 Erratum in: Proc Natl Acad Sci USA 1990 87(19):7797
20. Compton J Nucleic acid sequence-based amplification. Nature 1991, 7; 350(6313):91-92
21. Kwoh D Y, David G R, Whitfield K M, Chappelle H L, DiMichele L J, Gingeras T R Transcription-based amplification system and detection of amplified human immunodeficiency virus type 1 with a bead-based sandwich hybridization format. Proc Natl Acad Sci USA 1989, 86(4): 1173-1177

22. Walker G T, Fraiser M S, Schram J L, Little M C, Nadeau J G, Malinoswi D P Strand displacement amplification—an isothermal, in vitro DNA amplification technique. Nucleic Acids Res. 1992 11; 20(7): 1691-1696
23. Lomeli H, Tyagi S, Pritchard C G, Lizardi P M, Kramer F R Quantitative assays based on the use of replicatable hybridization probes. Clin Chem 1989, 35(9): 1826-1831
24. Matsukura M, Shinozuka K, Zon G, Mitsuya H, Reitz M, Cohen J S, Broder S Phosphorothioate analogs of oligodeoxynucleotides: inhibitors of replication and cytopathic effects of human immunodeficiency virus. Proc Natl Acad Sci USA 1987, 84(21):7706-7710
25. Egholm M, Buchardt O, Christensen L, Behrens C, Freier S M, Driver D A, Berg R H, Kim S K, Norden B, Nielsen P E PNA hybridizes to complementary oligonucleotides obeying the Watson-Crick hydrogen-bonding rules. Nature. 1993 Oct. 7; 365(6446):566-8
26. Asseline U, Delarue M, Lancelot G, Toulme F, Thuong N T, Montenay-Garestier T, Helene C Nucleic acid-binding molecules with high affinity and base sequence specificity: intercalating agents covalently linked to oligodeoxynucleotides. Proc Natl Acad Sci USA 1984, 81(11):3297-3301
27. Bej A K, Steffan R J, DiCesare J, Haff L, Atlas R M Detection of coliform bacteria in water by polymerase chain reaction and gene probes. Appl Environ Microbiol. 1990, 56(2):307-314
28. Bej A K, Mahbubani M H, Miller R, DiCesare J L, Haff L, Atlas R M Multiplex PCR amplification and immobilized capture probes for detection of bacterial pathogens and indicators in water. Mol Cell Probes 1990, 4(5):353-365

EXAMPLES

The following examples only serve to illustrate the present invention. These examples are in no way intended to limit the scope of the present invention.

Example 1

Sequence Analysis of PCR Products Covering Region A (FIG. 1) Derived from 25 Beta-PV Plasmid Clones Introduction
In order to use the PCR amplimers covering region A (FIG. 1) derived from the different beta-PV clones for the probe development their sequence was determined and compared to the reference sequences available on GenBank.
Materials and Methods
Sequence Analysis
First the PCR products were extracted from gel with the QIA Quick Gel Extraction Kit. Hereafter DNA sequence analysis was carried out according to the manual of the Big Dye Terminator Cycle Sequencing kit (v1) using the ABBI3100 Avant Genetic Analyzer (Applied Biosystems). The forward primers were used in this process that allowed reading of the sequence of the region A (FIG. 1).
Beta-PV Sequences from GenBank
The following accession numbers of HPV sequences were obtained from GenBank and used as a reference for the corresponding HPV genotype: HPV type 5: M17463; HPV type 8: M12737; HPV type 9: X74464; HPV type 12: X74466; HPV type 14: X74467; HPV type 15: X74468; HPV type 17: X74469; HPV type 19: X74470; HPV type 20: U31778; HPV type 21: U31779; HPV type 22: U31780; HPV type 23: U31781; HPV type 24: U31782; HPV type 25: X74471; HPV type 36: U31785; HPV type 37: U31786; HPV type 38: U31787; HPV type 47: M32305; HPV type 49: X74480; HPV type 75: Y15173; HPV type 76: Y15174; HPV type 80: Y15176; HPVcand92: AF531420; HPV93: AY382778; HPVcand96: AY382779.
Results
Upon comparison of the obtained sequences with the above mentioned references no differences were seen.
Discussion
The sequence analysis and the following comparison with the reference sequences showed that the amplimers could be used in the probe development.

Example 2

Identification of Different Beta-PV Types by Analysis of Region A (FIG. 1)

Introduction
Identification of the different beta-PV genotypes may have a great importance in elucidating the role of the beta-PVs in different diseases of the skin. Current beta-PV identification methods consist mainly of type specific PCR's or the cloning and sequencing of PCR products derived from broad spectrum beta-PV PCRs. Therefore, there is a clear need for a simple, rapid and reliable genotyping assay for the different beta-PV genotypes.
This assay should meet up to the following theoretical requirements:
1. The A Region (FIG. 1) should have Enough Sequence Variation for the 25 Beta-PV
genotypes to permit genotype specific detection and or identification.
This study looks into the intertypic sequence variation of the A region of 25 beta-PV types.
Materials and Methods
The A region of sequences from GenBank, mentioned in example 1, was used for phylogenetic analyses with the TREECON v1.3b software (Yves Van de Peer 1994, 1997).
Results
The constructed phylogenetic tree from the interprimer region is shown in FIG. 3. The intertypic sequence variation of this 83 bp region allows discrimination of all 25 beta-PVs.
Discussion
The region A heterogeneity, revealed in the phylogenetic analysis point to the aptness of the chosen PCR target for the development of a genotyping assay.

Example 3

Development of the Skin (Beta) HPV Genotyping Assay

Introduction
An aim of the invention was to develop an easy and reliable system for identification of beta-PV genotypes. The region A (FIG. 1) could be used for discrimination of 25 beta-PV genotypes. Sequence analysis of the PCR products is a very accurate method but not very suitable given the high prevalence of multiple infections. Hence we tried for a system that uses type-specific probes attached to a carrier (e.g. a nitrocellulose membrane) for the positive recognition and detection of the beta-PV genotypes.
Materials and Methods
Selection of Probes:
Based on the 83 bp sequences (region A FIG. 1), a number of type-specific probes were proposed. The probes are listed in Table 1.

Amplimers:

PCR amplimers derived form beta-PV plasmid clones with their sequence already confirmed by sequence analysis (as described in example 1) were utilized in the determination of the specificity of the probes.

Development of a Reverse Hybridization Format

A reverse hybridization assay (RHA) was chosen as platform for the test as it allows the analysis of multiple probes in a single hybridization step. One requirement that this kind of assay puts forward is that the probes should have very similar hybridization properties.

By way of an enzymatic reaction the oligonucleotide probes were given a 3' poly-(dT)

tail. 400 pmol oligonucleotide probe was incubated for 1 hour at 37° C. in 50 µl buffer containing 0.2M potassium cacodylate, 0.25 mM Tris-HCl (pH 6.6 at 25° C.), 0.25 mg/ml BSA, 2.5 mMCoCl$_2$, 3.2 mM dTTP (Pharmacia) and 200 U of recombinant Terminal Transferase (Roche). After a precipitation and a washing step with respectively 96% and 70% ethanol the pelleted oligonucleotide probe was dissolved in 50 µl of 6×SSC/0.002% lysamine (v/v). The concentration of these tailed oligonucleotide probe stocks was 8 pmol/µl. Dilutions of the tailed probes were immobilized on a nitrocellulose strip as parallel lines. As a control for the conjugate used in the RHA, biotinylated poly(dT)$_{40}$ was also applied.

The assay was performed in the Auto-LiPA system. Ten µl of the amplimer, biotin labelled via a 5' PCR primer modification was mixed with 10 µl Denaturation Solution (400 mM NaOH, 10 mM ethylenediaminetetraacetic acid (EDTA)) and 10 µl of a 50 pmol/µl oligo(d)T solution in a plastic trough containing the beta-PV strip. The mix was incubated for 5 minutes at room temperature. After the DNA denaturation step 2 ml of preheated Hybridization Solution, 3×SSC (1×SSC: 15 mM Na-citrate and 150 mM NaCl), 0.1% sodium dodecylsulphate (SDS), was added. The hybridization was carried out at 50° C. for 1 hour. The strips were then washed 3 times with 2 ml of preheated Stringent Wash Solution, 3×SSC, 0.1% SDS at 50° C. The first two washes take 3 minutes and the third 30 minutes. The next wash step used 2 ml Rinse Solution (phosphate buffer containing NaCl, Triton® and 0.05% methylisothiazolone (MIT)/0.48% chloroacetamide (CAA) and was performed at 50° C. Further steps were carried out at 27° C. First the strips were washed with 2 ml Rinse Solution. Subsequently the strips were incubated for 30 minutes with 2 ml Conjugate Buffer (phosphate buffer containing NaCl, Triton®, protein stabilisers and 0.01% MIT/0.1% CAA) containing alkaline phosphatase labelled streptavidin. Hereafter two wash steps with each 2 ml of Rinse Solution were performed. The next wash used 2 ml Substrate Buffer (Tris buffer containing NaCl and MgCl$_2$ and 0.01% MIT/0.1% CAA). Color development was achieved by incubation with Substrate Buffer containing bromochloroindolylphosphate (BCIP) and nitroblue tetrazolium (NBT) in dymethylformamide for 30 minutes. The reaction was stopped by washing for 3 and 10 minutes with Rinse Solution and after a last wash with water. The strips were dried and the purple colored bands were visually interpreted.

Results

For this experiment 25 type-specific probes as well as 2 other probes were selected for the simultaneous detection and discrimination of 25 beta-PV genotypes (preferred probes from table 1). Four probes for broad spectrum detection of beta-PV genotypes were also chosen (preferred probes from table 2). The outline of the strip is shown in FIG. 4 and typical patterns arising upon analysis of amplimers derived from the 25 beta-PV clones are depicted in FIG. 5.

In most cases the probe name is directly linked to the HPV type (e.g. a purple color on probe line HPV5 indicates the presence of HPV5, see probe HPV5, table 1). For HPV8 however, two probes play a role in its identification (probe HPV8I and probe HPV8 II). The HPV8 I probe could in an exceptional case show a weak cross-reaction with HPV 14, if present in very high copy numbers. This is due to limited sequence variation between the PCR product of HPV14 and the HPV8 I probe. To circumvent this problem probe HPV8 II was developed. It cannot cross react with HPV14 because of sufficient sequence differences between HPV 14 and HPV8 in the region of the amplimer that this probe targets. However, this is not a specific HPV8 probe since the HPV47 amplimer is homologous to probe HPV8 II. So to positively identify HPV8 preferably probe HPV8 I and probe HPV8 II should be positive or, due to a higher sensitivity only probe HPV8 II should be positive but then in absence of a reactive HPV47 probe. One of the restrictions of the test that arises here is the limited ability to detect the presence of HPV8 in a mixed infection with HPV14 and HPV47. A comparable problem arises with the genotyping of HVP type 21. Because it cannot be completely excluded that probe HPV21 will show cross reactivity with the amplimers of HPV 8 and HPV 14, probe cHPV21 has been developed. Probe cHPV 21 does not react with HPV8 or HPV 14 and so to positively identify HPV type 21 both probe HPV21 and probe cHPV 21 should be reactive. However the amplimers of both HPV20 and 22 will be reactive with probe cHPV 21, which could lead to a limited ability to detect the presence of HPV21 in a mixed infection of HPV8 or 14 with HPV20 or 22.

In summary, HPV genotypes 5, 9, 12, 14, 15, 17, 19, 23, 24, 25, 36, 37, 38, 49, 75, 76, 80, cand92, 93 and cand96 are recognized by hybridization to a single probe line, whereas HPV types 8, 20, 21, 22 and 47 yield a specific hybridization pattern on the RHA.

Discussion

The described beta-PV RHA detects and identifies simultaneously the HPV genotypes 5, 8, 9, 12, 14, 15, 17, 19, 20, 21, 22, 23, 24, 25, 36, 37, 38, 47, 49, 75, 76, 80, cand92, 93 and cand96. However, the RHA can be extended with other type-specific probes to identify so far unknown beta-PV genotypes.

In summary, the beta-PV RHA could be a useful tool to improve the molecular diagnosis and epidemiology of beta-PV infections, which presumably play a role in the etiology of non-melonoma skin cancers.

Example 4

Development of Universal Probes for the Skin (Beta) HPV Genotyping Assay

Introduction

In the beta-PV genus 25 established and candidate HPV types are present. Apart from these at least 35 new types can be added to the genus based upon partial L1 sequences (3). In light of the probable expansion of the genus the aim of this example was to develop universal beta-PV probes.

A relatively conserved region (region B, FIG. 1), was found suitable for development of universal probes. Four probes were selected to pick up the bulk of the known beta-PVs (preferred probes from table 2). After tailing they were mixed and applied as a single probe line. In a single infection of an unknown type, only a reactive universal probe line is present. In the current example it is shown that universal probes can be used for detection of so far unknown beta-PV types.

Methods

Possible universal probes are annoted in table 2. Samples analyzed with the beta-PV genotyping assay that only gave a reaction with the universal probeline and that showed a relatively strong band upon agarose gel electrophoresis were subjected to direct sequencing as described in example 1.

Results

Five sequences were found and compared to the available sequences in the GenBank database using the BLASTn program. No complete matches were found. However, for all but one sequence the first nearly matching sequences belong to the beta-PV genus. The sequence that did not give beta-PV hits with the BLASTn program was subjected to phylogenetic analysis. It appeared that it is a HPV sequence belonging to the beta-PVs (based on 80+/−nts).

Conclusion

With the universal probes DNA sequences from unknown HPV types, probably belonging to the beta genus can be detected.

Example 5

Reproducibility of the Skin (Beta) HPV Genotyping Assay

Introduction

The present example is intended to show the inter-laboratory variation of the assay.

Materials and Methods

A panel of 20 PCR products encompassing region A (FIG. 1) was exchanged between two laboratories. As a means to calculate the reproducibility, the genotyping results of the samples were compared and divided into identical results (both results are indistinguishable), compatible results (both results show at least one or more of the same genotype(s)) and discordant results (no similarities are found between both results).

Results and Conclusion

The genotyping results and comparisons of these with each other are indicated in table 3. The percentages of identical, compatible and discordant results are 55%, 40% and 5%, respectively. Given the high number of identical and compatible results, the assay can be considered as robust since it is highly reproducible in an inter-laboratory setting.

Example 6

Persistence of Beta-PV DNA in Plucked Eyebrows of Healthy Individuals

Introduction

The detection of beta-PV DNA is generally used as an epidemiological tool, but it is unknown whether detection of beta-PV DNA in plucked eyebrow hairs indicates the presence of passenger virus or a true infection. This example describes the persistent presence of a spectrum of beta-PV DNA types in the eyebrow hairs from 23 healthy individuals during twelve months.

Materials and Methods

Ten eyebrow hairs were plucked from 23 individuals. For each new sample a clean pair of tweezers was used to pluck the hairs. Special care was taken to check if all the hairs still had a hair bulb attached.

PCR products encompassing region A (FIG. 1) were analyzed by reverse hybridization as described in example 3, respectively.

Results

The genotyping results are depicted in tables 4.

Conclusion

The repetitive detection of type-identical beta-PV DNA in plucked eyebrow hairs over time suggests that the presence of the DNA generally indicates an infection and that the skin (beta) HPV genotyping assay can be used to detect these infections, even when multiple types are present.

TABLE 1

Beta-PV probes.

| probe | 5'-sequence-3' | SEQ ID NO: | polarity | position |
|---|---|---|---|---|
| HPV12* | GCCAACATGGAGAATC | 1 | + | 56 |
| HPV14* | GGGAGACAATGGAGAAT | 2 | + | 54 |
| 15 EV PR1 | GACACTTAGAGCTCAGTGAT | 3 | + | 23 |
| 15 EV PR2 | ACAGTTAGAGCTCAGTGAT | 4 | + | 24 |
| 15 EV PR3 | AGACAGTTAGAGCTCAGTG | 5 | + | 22 |
| 15 EV PR4 | GAGACAGTTAGAGCTCAGT | 6 | + | 21 |
| 15 EV PR5 | GAGACAGTTAGAGCTCAGC | 7 | + | 21 |
| 15 EV PR6 | GAGACAGTTAGAGCTCA | 8 | + | 21 |
| 15 EV PR7 | AGACAGTTAGAGCTCAG | 9 | + | 22 |
| HPV15* | AGACAGTTAGAGCTCA | 10 | + | 22 |
| HPV17* | GGCATCAGTTAGATCTGAG | 11 | + | 20 |
| HPV19* | TGGCAACAATTAGAACTG | 12 | + | 19 |
| 20 EV PR1 | GAAGCAATTAGAGCTGAGT | 13 | + | 21 |
| 20 EV PR2 | GAAGCAATTAGAGCTGAGG | 14 | + | 21 |
| 20 EV PR3 | TGGAAGCAATTAGAGCTG | 15 | + | 19 |

TABLE 1-continued

Beta-PV probes.

| probe | 5'-sequence-3' | SEQ ID NO: | polarity | position |
|---|---|---|---|---|
| HPV20* | GGAAGCAATTAGAGCTG | 16 | + | 20 |
| 21 EV PR1 | GAATCTCAGCGATCGT | 17 | + | 67 |
| 21 EV PR2 | GAATCTCAGCGATCGTGG | 18 | + | 67 |
| 21 EV PR3 | GAATCTCAGCGATCGTTG | 19 | + | 67 |
| 21 EV PRX RC | ATTCTCCATTTTCTCCCG | 20 | − | 70 |
| cHPV21* | ATTCTCCATTTTCTCCC | 21 | − | 70 |
| HPV21* | GAATCTCACCGATCGGGG | 22 | + | 67 |
| 21 EV PR12 | AGAATCTCAGCCATCCGGG | 23 | + | 66 |
| 21 EV PR11 RC | CGATCGCTGAGATTCC | 24 | − | 81 |
| 21 EV PR12 RC | GATCGCTGAGATTCT | 25 | − | 80 |
| 21 EV PR13 RC | ACGATCGCTGAGATTCC | 26 | − | 82 |
| 21 EV PR14 RC | AACGATCGCTGAGATTCC | 27 | − | 83 |
| 21 EV prX | GGGAGAAAATGGAGAAT | 28 | + | 54 |
| HPV22* | GAGAAAATGGAGAAACTCA | 29 | + | 56 |
| HPV23* | TGGATACAATTAGGACTCAG | 30 | + | 19 |
| 24 EV PR1 | AGAGGATGGAGAACCTG | 31 | + | 57 |
| HPV24* | GAGAGGATGGAGAACCTG | 32 | + | 56 |
| 24 EV PR3 | AGAGGATGGAGAACCTGA | 33 | + | 57 |
| 25 EV PR1 | GGCATCAATTAGACCTG | 34 | + | 20 |
| HPV25* | TGGCATCAATTAGACCTG | 35 | + | 19 |
| 25 EV PR3 | GGCATCAATTAGACCTGA | 36 | + | 20 |
| 36 EV PR1 | GAACTCAGTGACCAAGAAG | 37 | + | 31 |
| 36 EV PR2 | GAACTCAGTGACCAAGAA | 38 | + | 31 |
| 36 EV PR3 | AGAACTCAGTGACCAAGA | 39 | + | 30 |
| 36 EV PR4 | GAACTCAGTGACCAAGA | 40 | + | 31 |
| 36 EV PR11 | GAACTCAGTGACCAAG | 41 | + | 31 |
| 36 EV PR12 | AGAACTCAGTGACCAA | 42 | + | 30 |
| HPV36* | TAGAACTCAGTGACCAA | 43 | + | 29 |
| 37 EV PR1 | GATCTCACTGACCAAGAAG | 44 | + | 31 |
| 37 EV PR2 | GATCTCACTGACCAAGAA | 45 | + | 31 |
| 37 EV PR3 | AGATCTCAGTGACCAAGA | 46 | + | 30 |
| 37 EV PR4 | GATCTCAGTGACCAAGA | 47 | + | 31 |
| HPV37* | GATCTCAGTGACCAAG | 48 | + | 31 |
| 37 EV PR12 | AGATCTCAGTGACCAA | 49 | + | 30 |
| 37 EV PR13 | TAGATCTCAGTGACCAA | 50 | + | 29 |
| HPV38* | GGGAGACAATGGAAACT | 51 | + | 54 |
| HPV47* | TGGACACACTTAGACCTG | 52 | + | 19 |
| 47 EV PR1.CH | GCTGGACACACTTAGACCTG | 53 | + | 19 |

TABLE 1-continued

Beta-PV probes.

| probe | 5'-sequence-3' | SEQ ID NO: | polarity | position |
|---|---|---|---|---|
| 47 EV PR1RC.CH | GCAGGTCTAAGTGTGTCCA | 54 | − | 36 |
| 47 EV PR2.CH | GCGGGACACACTTAGACCTG | 55 | + | 20 |
| 47 EV PR3.CH | GCTGGACACACTTAGACCT | 56 | + | 19 |
| 49 EV PR1 | GAGCTCAGTGACCCAG | 57 | + | 31 |
| 49 EV PR10 | GAGGCACTCAACGCT | 58 | + | 65 |
| 49 EV PR11 | AGGCACTCAACGCTC | 59 | + | 66 |
| HPV49* | AGGCACTCAACGCTCTGG | 60 | + | 66 |
| HPV5* | GACCTGACTGATCAAGAA | 61 | + | 31 |
| 5 EV PR2.CH | GGGGACCTGAGTGATCAAGAA | 62 | + | 31 |
| 5 EV PR3 | AGACCTGAGTGATCAAGA | 63 | + | 30 |
| 5 EV PR1 | GACCTGAGTGATCAAGAAG | 64 | + | 31 |
| 5 EV PR2RC.CH | GTTTCTTGATCACTCAGGTC | 65 | − | 48 |
| 5 EV PR4.CH | GGGGACCTGAGTGATCAAGA | 66 | + | 31 |
| 5 EV PR5.CH | GGGCACCTGAGTGATCAAGAA | 67 | + | 32 |
| HPV75* | GAACTGAGTGATCCTGAAG | 68 | + | 31 |
| HPV76* | AGATCTCAGTGACCCTGA | 69 | + | 30 |
| 8 EV PR4 | ATTAGAGCTGAGTGATCAG | 70 | + | 27 |
| HPV8 I* | TTAGAGCTGAGTGATCAG | 71 | + | 28 |
| 8 EV PR5.CH | TTAGAGCTGAGTGATCA | 72 | + | 28 |
| 8 EV PR5RC.CH | GGTCTGATCACTCAGCTCTAA | 73 | − | 44 |
| 8 EV PR6.CH | TTAGAGCTGAGTGATC | 74 | + | 28 |
| 8 EV PR7.CH | GTAGAGCTGAGTGATCA | 75 | + | 29 |
| 8 EV PR1 | ATTAGAGCTGAGTGATCAAG | 76 | + | 27 |
| 8 EV PR10 | ACACAATTAGAGCTGAGTG | 77 | + | 22 |
| 8 EV PR11 | CACAATTAGAGCTGAGTGAG | 78 | + | 23 |
| 8 EV PR12 | CACAATTAGAGCTGAGTG | 79 | + | 23 |
| 8 EV PR13 | CACAATTAGAGCTGAGT | 80 | + | 23 |
| 8 EV PR14 | ACACAATTAGAGCTGAGT | 81 | + | 22 |
| 8 EV PR15 | ACACAATTAGAGCTGAGG | 82 | + | 22 |
| 8 EV PR2 | ATTAGAGCTGAGTGATCAA | 83 | + | 27 |
| 8 EV PR3 | TTAGAGCTGAGTGATCAAG | 84 | + | 28 |
| HPV8 II* | CCGAACATGGAGAATCT | 85 | + | 56 |
| 8 EV PRX2 | GCGAACATGGAGAATCG | 86 | + | 56 |
| 8 EV PR12 RC | CACTCAGCTCTAATTGTGC | 87 | − | 40 |
| 8 EV PR5 RC | TGATCACTCAGCTCTAAG | 88 | − | 44 |
| HPV80* | TAGATCTCAGTGATCACGA | 89 | + | 29 |
| HPV9* | GAGGATGGAAACTCTCAG | 90 | + | 56 |
| 92 EV PR1 | CAAAGGCTTTGGAGG | 91 | + | 10 |

TABLE 1-continued

Beta-PV probes.

| probe | 5'-sequence-3' | SEQ ID NO: | polarity | position |
|---|---|---|---|---|
| 92 EV PR10 | CGAGGGTGAGGATGG | 92 | + | 51 |
| HPV92* | AGGCTCTCACCGACC | 93 | + | 66 |
| HPV93* | CGAGACTCTGAGAGAAC | 94 | + | 64 |
| 96 EV PR1 | CGAGGGGAGGATG | 95 | + | 51 |
| HPV96* | GAGGCTCTGAACCAGC | 96 | + | 65 |

Selection of probes specifically hybridizing to the region from position 2662-2744 (numbers according to HPV type 5 sequence PPH5CG, GenBank accession number M17463). Preferred probes are indicated with an "*". "+" indicates a sense probe; "−" refers to an antisense probe. Underlined residues correspond to non beta-PV type-specific nucleotides. The column "position" indicates the corresponding position of the probe on the amplimer as seen from the 5'end of the probe. Underlined residues are not used in the determination of the position of the probe binding site.

TABLE 2

Universal beta-PV probes.

| probe | 5'-sequence-3' | SEQ ID NO: | polarity | position | Beta-PV types recognized |
|---|---|---|---|---|---|
| UniEV PR1* | TCTTTTTTTACAAGGCTTTGG | 97 | + | 1 | 5, 8, 14, 19-21, 25, 47, 93 |
| UniEV PR2* | TCTTTTTTTGAAAGGCTTTGG | 98 | + | 1 | 8, 9, 12, 15, 17, 22-24, 36, 37, 49, 75, 76, 80 |
| UniEV PR3* | TCTTTTTTTAAAAGGCTTTGG | 99 | + | 1 | 5, 8, 9, 19-25, 75, 76 |
| UniEV PR4* | TCTTTCTTTAAAAGGCTTTGG | 100 | + | 1 | 14 |
| UniEVPR1A | TCTTTTTTTACAAGGCTTTGGAC | 101 | + | 1 | 5, 8, 9, 12, 14, 19-25, 36, 37, 47, 49, 75, 76, 93 |
| UniEVPR1B | TCTTTTTTTACAAGGCTTTGGAA | 102 | + | 1 | 5, 8, 14, 19-21, 25, 47, 76 |

Selection of universal probes specifically hybridizing to region B from position 2662-2684 (numbers according to HPV type 5 sequence PPH5CG, GenBank accession number M17463). Preferred probes are indicated with "*". "+" indicates a sense probe.

TABLE 3

Inter-laboratory reproducibility of the RHA in a panel of 20 PCR products.

| sample | RHA Location 1 | Location 2 | Reproducibility |
|---|---|---|---|
| 1 | 23 | 23 | i |
| 2 | 23, 93 | 23, 38, 93 | c |
| 3 | 8, 20, 23, 38, 49, 92 | 8, 20, 23, 38, 49, 92 | i |
| 4 | — | 36 | d |
| 5 | 23, 80 | 23, 80 | i |
| 6 | 12, 14, 19, 23 | 12, 14, 19, 23 | i |
| 7 | 12, 14, 19, 23, 25 | 12, 14, 15, 19, 23, 25 | c |
| 8 | 14, 17, 38, 93 | 14, 38, 93 | c |
| 9 | 12, 23, 24, 80 | 12, 23, 24, 80 | i |
| 10 | 14, 19 | 14, 19 | i |
| 11 | — | — | i |
| 12 | 5, 17, 23, 93 | 5, 23, 93 | c |
| 13 | 8, 9, 15, 20, 23, 38, 49, 92 | 8, 15, 20, 23, 38, 49, 92 | c |
| 14 | 19, 38 | 19, 38 | i |
| 15 | 80 | 80 | i |
| 16 | 8, 38 | 8, 38 | i |
| 17 | 23 | 38, 23 | c |
| 18 | — | — | i |
| 19 | 12, 93 | 5, 8, 12, 93 | c |
| 20 | 12, 17, 23, 24, 80 | 5, 12, 15, 17, 23, 24, 25, 36, 37, 47, 80, 93 | c |

The PCR products were obtained from eyebrow hair samples from healthy individuals. The intra-laboratory reproducibility is divided into identical results (both results are indistinguishable), compatible results (both results show at least one or more of the same genotype(s)) and discordant results (no similarities are found between both results).

TABLE 4

HPV types detected in eyebrow hairs of 23 healthy individuals at 7 time points.

| Individual | Month 1 | 2 | 3 | 4 | 5 | 6 | 12 |
|---|---|---|---|---|---|---|---|
| 1 | — | — | — | 19 | 19 | 19 | — |
| 2 | 5, 23, 38, 76 | 8, 15, 23, 38 | 23, 38 | 15, 38 | 15, 38 | 38 | — |
| 3 | — | 15 | — | — | 23, 37 | 15, 23 | — |
| 4 | — | 8, 23 | 23 | — | — | 23 | — |

TABLE 4-continued

HPV types detected in eyebrow hairs of 23 healthy individuals at 7 time points.

| Individual | Month 1 | 2 | 3 | 4 | 5 | 6 | 12 |
|---|---|---|---|---|---|---|---|
| 5 | 8, 23, 24, 92 | 8, 23, 24, 75, 80, 92 | 8, 23, 24, 75, 93 | 8, 24 | 8, 23 | 8, 23, 24, 75 | 24 |
| 6 | — | — | — | — | — | — | — |
| 7 | — | 25 | 25 | 25 | 25 | — | — |
| 8 | — | 38 | — | 8, 38 | — | 8 | — |
| 9 | — | — | 23 | — | — | 23 | — |
| 10 | — | — | 9 | 23 | — | 9 | 23 |
| 11 | | — | 8 | — | — | — | — |
| 12 | — | — | 19, 93 | 23 | 9, 23 | — | 22 |
| 13 | 23, 93 | 17, 23, 93 | 5, 23, 24, 93 | 5, 23, 93 | 23, 93 | 5, 23, 93 | 5, 23 |
| 14 | 20, 23, 38, 49, 92 | 8, 9, 15, 20, 23, 38, 49, 92 | 8, 9, 14, 17, 20, 23, 38, 49, 92 | 8, 9, 15, 20, 23, 38, 92 | 20, 23, 38, 49, 92 | 8, 9, 15, 17, 20, 23, 38, 49, 92 | 8, 9, 15, 20, 23, 38, 92 |
| 15 | — | — | — | 12 | — | 17, 23, 38 | 9, 12, 17 |
| 16 | 23, 80 | 80 | 14, 23, 80 | 14, 80 | 23, 24, 80 | 23, 80 | 23 |
| 17 | 12, 14, 19, 23 | 8, 38 | 19, 23, 38 | 5, 23, 38 | 23, 96 | 23, 38 | 9, 14, 17, 23, 36, 49 |
| 18 | 12, 14, 19, 23, 25 | 23 | 19, 23, 76 | 19 | — | 24, 93 | — |
| 19 | 14, 17, 38, 93 | 12, 93 | 12, 14, 93 | 38, 93 | 93 | — | 93 |
| 20 | 12, 23, 24, 80 | 12, 17, 23, 24, 80 | 12, 23, 24, 80 | 12, 17, 19, 23, 24, 80, 93 | 12, 23, 24, 80 | 12, 23, 24, 80 | 12, 17, 23, 24, 80 |
| 21 | 5, 17, 20, 23, 80 | 5, 20, 23 | 5, 20, 23 | 5, 20 | 5, 20 | 5, 20 | 5, 20, 23 |
| 22 | 23, 93 | 8, 12, 17, 80 | 14 | 17, 19 | 23 | — | 17 |
| 23 | 5, 15, 23, 25, 36, 37 | 5, 15, 23, 25, 37 | 5, 15, 23, 25, 36, 37 | 5, 8, 15, 23, 25, 36, 37 | 5, 8, 15, 23, 25, 36, 37 | 5, 25, 37 | 5, 15, 23, 25, 36, 37 |

The invention claimed is:

1. A method for identifying the type of any beta-PV nucleic acid among types 5, 8, 9, 12, 14, 15, 17, 19-25, 36-38, 47, 49, 75, 76, 80, 92, 93 and 96 present in a sample, the method comprising the steps of:
   (i) contacting said sample with the probes of SEQ ID NOS:1, 2, 10, 11, 12, 16, 21, 22, 29, 30, 32, 35, 43, 48, 51, 52, 60, 61, 68, 69, 71, 85, 89, 90, 93, 94 and 96 and obtaining a hybridization result whereby at least one hybrid complex is formed, and
   (ii) identifying the type of beta-PV present in the sample based on analysis of the hybridization result.

2. The method of claim 1 wherein any beta-PV nucleic acid present in the sample is amplified prior to said contacting.

3. The method of claim 1 wherein the presence of beta-PV nucleic acid in the sample is confirmed prior to obtaining said hybridization result.

4. The method of claim 1 wherein the hybridisation result is obtained in the presence of a solid support.

5. The method of claim 4 wherein the probes are coupled to beads.

6. The method of claim 1 which further comprises contacting said sample with at least one additional probe selected from the group consisting of SEQ ID NOS:97, 98, 99 and 100, to confirm the presence of beta-PV nucleic acid in the sample.

7. A method for identifying the type of any beta-PV nucleic acid among types 5, 8, 12, 14, 19, 20, 21, 24, 25, 36, 47 and 93 present in a sample, the method comprising the steps of:

(i) contacting said sample with the probes of SEQ ID NOS:1, 2, 12, 16, 21, 22, 32, 35, 43, 52, 61, 71, 85, and 94, and obtaining a hybridization result whereby at least one hybrid complex is formed, and (ii) identifying the type of beta-PV present in the sample based on analysis of the hybridization result.

8. The method of claim 7 wherein any beta-PV nucleic acid present in the sample is amplified prior to said contacting.

9. The method of claim 7 wherein the presence of beta-PV nucleic acid in the sample is confirmed prior to the said identifying.

10. The method of claim 7 wherein the hybridisation result is obtained in the presence of a solid support.

11. The method of claim 10 wherein the probes are coupled to beads.

12. The method of claim 7 which further comprises contacting said sample with at least one additional probe selected from the group consisting of SEQ ID NOS:97, 98, 99 and 100, to confirm the presence of beta-PV nucleic acid in the sample.

13. The method of claim 12 which comprises contacting said sample with the probes SEQ ID NO:97, 98, 99 and 100.

* * * * *